US010196435B2

(12) United States Patent
Epstein et al.

(10) Patent No.: US 10,196,435 B2
(45) Date of Patent: Feb. 5, 2019

(54) OX40L FUSION PROTEIN FOR THE IMMUNOTHERAPY OF TUMORS OF VETERINARY ANIMALS

(71) Applicants: Alan L. Epstein, Pasadena, CA (US); Peisheng Hu, Covina, CA (US)

(72) Inventors: Alan L. Epstein, Pasadena, CA (US); Peisheng Hu, Covina, CA (US); John Ohlfest, Roseville, MN (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 14/543,714

(22) Filed: Nov. 17, 2014

(65) Prior Publication Data
US 2015/0191525 A1 Jul. 9, 2015

Related U.S. Application Data

(60) Provisional application No. 61/905,641, filed on Nov. 18, 2013.

(51) Int. Cl.
C07K 14/705 (2006.01)
A61K 39/00 (2006.01)
C07K 14/575 (2006.01)
A61K 39/39 (2006.01)
A61K 38/00 (2006.01)

(52) U.S. Cl.
CPC .... C07K 14/70578 (2013.01); A61K 39/0011 (2013.01); A61K 39/39 (2013.01); C07K 14/575 (2013.01); C07K 14/70575 (2013.01); A61K 38/00 (2013.01); A61K 2039/552 (2013.01); A61K 2039/55516 (2013.01); A61K 2039/55561 (2013.01); C07K 2319/02 (2013.01); C07K 2319/30 (2013.01)

(58) Field of Classification Search
None
See application file for complete search history.

(56) References Cited

U.S. PATENT DOCUMENTS 7,595,305 B2 * 9/2009 Agrawal ............... C07H 21/00 514/44 R
2013/0209511 A1 * 8/2013 Mebatsion ........... A61K 39/008 424/209.1

FOREIGN PATENT DOCUMENTS

WO  WO-2010/117760 A2 * 10/2010
WO  WO-2011/027310 A1 * 3/2011

OTHER PUBLICATIONS

Murphy K A et al. (2012), "An in Vivo Immunotherapy Screen of Costimulatory Molecules Identifies Fc-OX40L as a Potent Reagent for the Treatment of Established Murine Gliomas", Clin Cancer Res 2012; 18:4657-4668.
Murphy K A et al. (2014), "CD8 T cell-independent tumor regression induced by Fc-OX40L and therapeutic vaccination in a mouse model of glioma", J Immunol. 2014, 192(1):224-33, Epub Nov. 29, 2013.

* cited by examiner

Primary Examiner — Alana Harris Dent
(74) Attorney, Agent, or Firm — Foley & Lardner LLP; Antoinette F. Konski; Natasha Iyer

(57) ABSTRACT

Provided is an isolated recombinant polypeptide comprising an immunoglobulin domain and a canine OX40L extracellular domain polypeptide fragment or a biological equivalent thereof and compositions comprising: an isolated recombinant polypeptide comprising an immunoglobulin domain and a canine OX40L extracellular domain polypeptide fragment; and a pharmaceutically acceptable carrier. Also provided are methods for treating or ameliorating the symptoms of cancer in a canine comprising administering an effective amount of the isolated recombinant polypeptide of the disclosure and/or a composition of the disclosure to a canine in need thereof.

8 Claims, 9 Drawing Sheets

Specification includes a Sequence Listing.

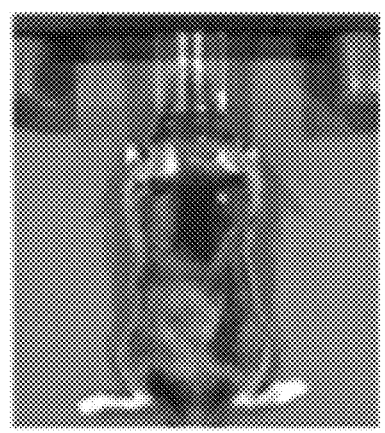
FIG. 1B

ATGCTGTTGCTGGGAGCTGTTCTACTGCTATTAGCTCTGCCCGGTCATGACCAGGAA
ACCACGACTCAAGGGCCCGGAGTCCTGCTTCCCCTGCCCAAGGGGGCCTGCACAGG
TTGGATGGCGGGCATCCCAGGGCATCCGGGCCATAATGGGGCCCCAGGCCGTGATG
GCAGAGATGGCACCCCTGGTGAGAAGGGTGAGAAAGGAGATCCAGGTCTTATTGGT
CCTAAGGGAGACATCGGTGAAACCGGAGTACCCGGGGCTGAAGGTCCCCGAGGCTT
TCCGGGAATCCAAGGCAGGAAAGGAGAACCTGGAGATACACCCCATGCCCAGTCC
CTGAACCTCTGGGAGGGCCTTCGGTCCTCATCTTTCCCCCGAAACCCAAGGACATCC
TCAGGATTACCCGAACACCCGAGGTCACCTGTGTGGTGTTAGATCTGGGCCGTGAGG
ACCCTGAGGTGCAGATCAGCTGGTTCGTGGATGGTAAGGAGGTGCACACAGCCAAG
ACCCAGTCTCGTGAGCAGCAGTTCAACGGCACCTACCGTGTGGTCAGCGTCCTCCCC
ATTGAGCACCAGGACTGGCTCACAGGGAAGGAGTTCAAGTGCAGAGTCAACCACAT
AGACCTCCCGTCTCCCATCGAGAGGACCATCTCTAAGGCCAGAGGGAGGGCCCATA
AGCCCAGTGTGTATGTCCTGCCGCCATCCCCAAAGGAGTTGTCATCCAGTGACACAG
TCAGCATCACCTGCCTGATAAAAGACTTCTACCCACCTGACATTGATGTGGAGTGGC
AGAGCAATGGACAGCAGGAGCCCGAGAGGAAGCACCGCATGACCCCGCCCCAGCT
GGACGAGGACGGGTCCTACTTCCTGTACAGCAAGCTCTCTGTGGACAAGAGCCGCT
GGCAGCAGGGAGACCCCTTCACATGTGCGGTGATGCATGAAACTCTACAGAACCAC
TACACAGATCTATCCCTCTCCCATTCTCCGGGTAAACAGGTGCCGCCTCAGTATCCT
CCAATTCAAAGTATCAGAGTACAATTTACCAGGTGTGAGAATGAGAAAGGTTGCAT
CATCACATCCCCAAGCAAGGATGAAACTATGAAGGTGCAAGACAACTCAATCATCA
TTAACTGTGATGGGTTTTATCTCATCTCCCTGAAGGGTTACTTCTCTGAGGAGCTCAG
CCTCAGCCTTTATTACCGAAAGGGTCGGGGACCCCTCTTCTCTCTGAGCAAGGTCAC
ATCTGTTGACTCCATTGGAGTGGCCTATCTGGCTTTCAAGGACAAAGTCTACTTTAAT
GTGACCACTCACAGTACCTCCTACAAAGACATCCAGGTGAATGGTGGGGAATTGATT
CTCATTCATCAAAATCCTGGTGGCTTCTGTGCCTACTGA

FIG. 2

MLLLGAVLLLLALPGHDQETTTQGPGVLLPMLLLGAVLLLLALPGHDQETTTQGPGVLL
PLPKGACTGWMAGIPGHPGHNGAPGRDGRDGLPKGACTGWMAGIPGHPGHNGAPGRD
GRDGTPGEKGEKGDPGLIGPKGDIGETGVPGAEGTPGEKGEKGDPGLIGPKGDIGETGVP
GAEGPRGFPGIQGRKGEPGDTPPCPVPEPLGGPSDTPPCPVPEPPRGFPGIQGRKGEPGVLI
FPPKPKDILRITRTPEVTCVVLDLGREDPEVQISWFVDGKEVHTAKTQSREQQFNGTYRV
VSVLPIEHQDWLTGKEFKCRVNHIDLPSPIERTISKARGRAHKPSVYVLPPSPKELSSSDT
VSITCLIKDFYPPDIDVEWQSNGQQEPERKHRMTPPQLDEDGSYFLYSKLSVDKSRWQQ
GDPFTCAVMHETLQNHYTDLSLSHSPGKQVPPQYPPIQSIRVQFTRCENEKGCIITSQVPP
QYPPIQSIRVQFTRCENEKGCIITSPSKDETMKVQDNSIIINCDGFYLISLKGYFPSKDETM
KVQDNSIIINCDGFYLISLKGYFSEELSLSLYYRKGRGPLFSLSKVTSVDSIGSEELSLSLY
YRKGRGPLFSLSKVTSVDSIGVAYLAFKDKVYFNVTTHSTSYKDIQVNGGEVAYLAFKD
KVYFNVTTHSTSYKDIQVNGGELILIHQNPGGFCAY

FIG. 3

ADP-caFc-caOX40L

MLLLGAVLLLLALPGHDQETTTQGPGVLLPLPKGACTGWMAGIPGHPGHNGAPGRDGR
DGTPGEKGEKGDPGLIGPKGDIGETGVPGAEGPRGFPGIQGRKGEPG
DTPPCPVPEPLGGPSVLIFPPKPKDILRITRTPEVTCVVLDLGREDPEVQISWFVDGKEVH
TAKTQSREQQFNGTYRVVSVLPIEHQDWLTGKEFKCRVNHIDLPSPIERTISKARGRAHK
PSVYVLPPSPKELSSSDTVSITCLIKDFYPPDIDVEWQSNGQQEPERKHRMTPPQLDEDGS
YFLYSKLSVDKSRWQQGDPFTCAVMHETLQNHYTDLSLSHSPGKQVPPQYPPIQSIRVQ
FTRCENEKGCIITSPSKDETMKVQDNSIIINCDGFYLISLKGYFSEELSLSLYYRKGRGPLF
SLSKVTSVDSIGVAYLAFKDKVYFNVTTHSTSYKDIQVNGGELILIHQNPGGFCAY

Blac: ADP domain

Red: Dog IgGA Fc region

Blue: Canis OX40L extracellular domain

FIG. 4

OX40L FUSION PROTEIN FOR THE IMMUNOTHERAPY OF TUMORS OF VETERINARY ANIMALS

CROSS-REFERENCE TO RELATED APPLICATION

This application claims the benefit under 35 U.S.C. § 119(e) of U.S. Provisional Application No. 61/905,641, filed Nov. 18, 2013, the content of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Feb. 10, 2015, is named 108578-6602_SL.txt and is 13,225 bytes in size.

STATEMENT OF GOVERNMENT SUPPORT

This invention was made with government support under Grant No. 1R21NS070955-01 awarded by National Institutes of Health, National Institute of Neurological Disorders and Stroke (NIH/NINDS). The government has certain rights in the invention.

TECHNICAL FIELD

The present disclosure relates to cancer immunotherapeutic compositions and methods.

BACKGROUND

The following discussion of the background of the disclosure is merely provided to aid the reader in understanding the disclosure and is not admitted to describe or constitute prior art to the present disclosure.

Cancer of veterinary animals, such as canine cancer, affects one out of every three dogs. Of those, over half of them will die of cancer. Unfortunately, at this time, there is no true cure (100% remission) for most tumors in dogs. For example, brain tumors are generally considered to be malignant due to the delicate and poorly regenerative nature of neurons and restriction of the brain to the finite space of the cranium which does not allow tumor growth devoid of collateral damage to brain parenchyma. Therefore, general long-term prognosis for canine brain tumors is poor. Current treatment of canine tumors revolves around four main modalities: surgery, radiation, chemotherapy, and palliative (pain relieving) care. Depending on the type, extent, and location of the cancer, any one or combination of these techniques may be employed. While these treatments may help to some extent, there is a need in the art for more effective therapies that can be used alone or in combination with traditional therapies for the treatment of veterinary cancer.

SUMMARY

Provided are new cancer immunotherapeutic methods and compositions for the treatment of canines.

Aspects of the disclosure relate to an isolated recombinant polypeptide comprising, or alternatively consisting essentially of, or yet further consisting of, an immunoglobulin domain and a canine OX40L extracellular domain polypeptide, wherein the canine OX40L extracellular domain polypeptide comprises, or alternatively consists essentially of, or yet further consists of, from about amino acid 447 to about amino acid 698 of a polypeptide of SEQ ID NO: 2 as shown in FIG. 3, or from about amino acid 332 to about amino acid 464 of a polypeptide of SEQ ID NO: 3, as shown in FIG. 4, or a biological equivalent of each thereof. OX40L is a co-stimulatory receptor expressed on $CD4^+$ and $CD8^+$ T cells that promotes survival, proliferation, and generation of memory while simultaneously inhibiting the suppressive function of regulatory T cells.

An additional aspect of the disclosure relates to an isolated recombinant polypeptide comprising, or alternatively consisting essentially of, or yet further consisting of SEQ ID NO: 2 (FIG. 3), or SEQ ID NO: 3 (FIG. 4), or a biological equivalent of each thereof. Further aspects relate to a composition comprising, or alternatively consisting essentially of, or yet further consisting of:

a) an isolated recombinant polypeptide comprising, or alternatively consisting essentially, of or yet consisting of, an immunoglobulin domain and a canine OX40L extracellular domain polypeptide; and b) a pharmaceutically acceptable carrier.

Kits comprising, or alternatively consisting essentially of, or yet further consisting of a) an isolated recombinant polypeptide disclosed herein comprising or alternatively consisting essentially of, or yet further consisting of an immunoglobulin domain and a canine OX40L extracellular domain polypeptide and b) a pharmaceutically acceptable carrier.

Other aspects relate to an isolated polynucleotide encoding an isolated recombinant polypeptide comprising or alternatively consisting essentially of, or yet further consisting of, an immunoglobulin domain and a canine OX40L extracellular domain polypeptide as described herein. Also disclosed are methods for preparing the therapeutic compositions and isolating the therapeutic polypeptides.

Method aspects of the disclosure relate to a method for treating or ameliorating the symptoms of cancer in a canine comprising, or alternatively consisting essentially of, or yet further consisting of administering an effective amount of an isolated recombinant polypeptide described herein and/or a composition described herein to a canine in need thereof. Further method aspects relate to a method for enhancing a tumor suppressive therapy in a canine in need thereof, comprising administering an effective amount of an isolated recombinant polypeptide described herein and/or a composition described herein.

BRIEF DESCRIPTION OF THE FIGURES

FIGS. 1A-1C demonstrate the synergy between tumor cell vaccine and OX40L in murine glioblastomas. FIG. 1A shows that B6 mice were implanted with intracerebral GL261-Luc glioma cells and treated when tumors were well established on day 7. Vaccination (GL261 lysates from 20% $O_2$ cultures plus CpG ODN as adjuvant) was given on days 7, 10, and 13. Recombinant mouse OX40L was administered on days 7, 10, and 13, or was given in combination with vaccination. N=5-6/group; statistics by log-rank test). FIG. 1B shows that representative bioluminescence imaging shows complete tumor regression on combination group. FIG. 1C shows immunofluorescence data from flank tumor model demonstrating that OX40L monotherapy increases expression of VCAM-1, which is crucial for T cell infiltration from tumor capillaries into tumor mass.

FIG. 2 shows the nucleotide sequence of the synthetic fusion gene (SEQ ID NO: 1) that can be used to produce the recombinant polypeptide. The synthetic gene consists of the following sequence: human ADP signal peptide+collagen like domain (1-315), Canis IgG A Fc region (316-993), and Canis OX40L extracellular domain (994-1395). This polynucleotide sequence encodes a polypeptide of this disclosure.

FIG. 3 shows the amino acid sequence of ADP-Fc-cOX40L fusion protein (SEQ ID NO: 2). The amino acid sequence of the fusion protein consisted of ADP signal peptide+collagen like domain (1-195), Canis IgG A Fc region (1196-446), and Canis OX40L extracellular domain (447-698).

FIG. 4 shows another amino acid sequence of ADP-Fc-cOX40L fusion protein (SEQ ID NO: 3). The amino acid sequence of the fusion protein consisted of ADP signal peptide+collagen like domain (1-105), Canis IgG A Fc region (106-331), and Canis OX40L extracellular domain (332-464).

DETAILED DESCRIPTION

Definitions

Figure 1A:
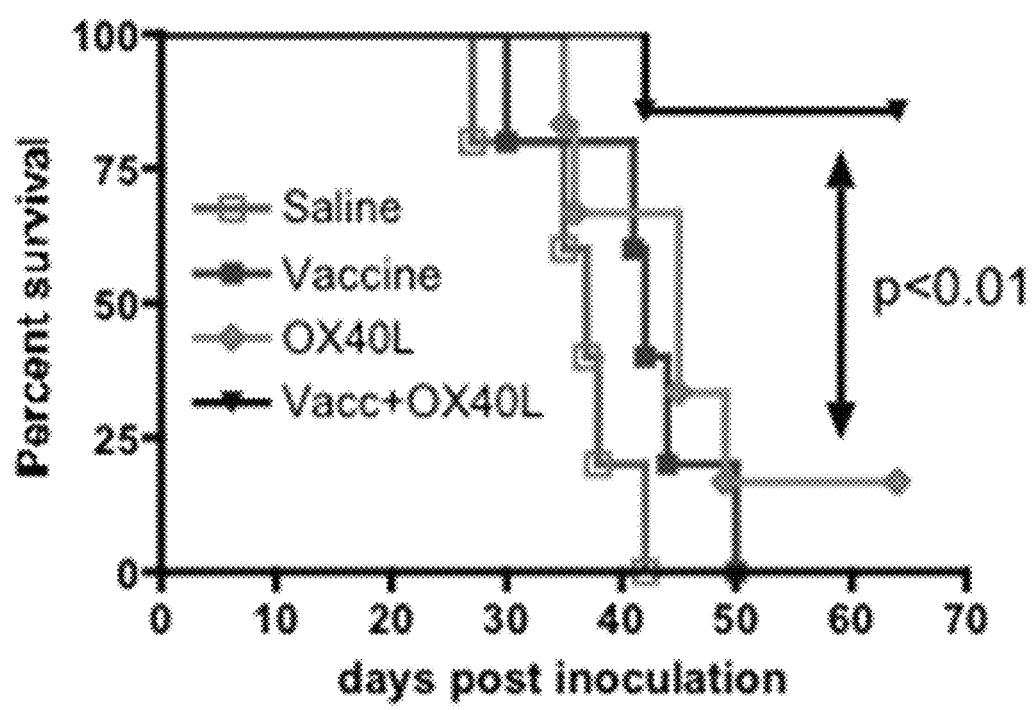

Throughout this disclosure, various publications, patents and published patent specifications are referenced by an identifying citation. The disclosures of these publications, patents and published patent specifications are hereby incorporated by reference in their entirety into the present disclosure.

Before the compositions and methods are described, it is to be understood that the disclosure is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

The practice of the present disclosure will employ, unless otherwise indicated, conventional techniques of tissue culture, immunology, molecular biology, microbiology, cell biology and recombinant DNA, which are within the skill of the art. See, e.g., Sambrook et al., (1989) Molecular Cloning: A Laboratory Manual, 2nd edition; Ausubel et al., eds. (1987) Current Protocols In Molecular Biology; MacPherson, B. D. Hames and G. R. Taylor eds., (1995) PCR 2: A Practical Approach; Harlow and Lane, eds. (1988) Antibodies, A Laboratory Manual; Harlow and Lane, eds. (1999) Using Antibodies, a Laboratory Manual; and R.I. Freshney, ed. (1987) Animal Cell Culture.

All numerical designations, e.g., pH, temperature, time, concentration, and molecular weight, including ranges, are approximations which are varied (+) or (−) by increments of 1.0 or 0.1, as appropriate. It is to be understood, although not always explicitly stated that all numerical designations are preceded by the term "about". It also is to be understood, although not always explicitly stated, that the reagents described herein are merely exemplary and that equivalents of such are known in the art.

As used in the specification and claims, the singular form "a," "an" and "the" include plural references unless the context clearly dictates otherwise.

As used herein, the term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of" shall mean excluding more than trace elements of other ingredients and substantial method steps. Embodiments defined by each of these transition terms are within the scope of this invention.

A "composition" is also intended to encompass a combination of active agent and another carrier, e.g., compound or composition, inert (for example, a detectable agent or label) or active, such as an adjuvant, diluent, binder, stabilizer, buffers, salts, lipophilic solvents, preservative, or the like. Carriers also include pharmaceutical excipients and additives, proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

A "pharmaceutical composition" is intended to include the combination of an active agent with a carrier, inert or active, making the composition suitable for diagnostic or therapeutic use in vitro, in vivo or ex vivo.

The term "pharmaceutically acceptable carrier" (or medium), which may be used interchangeably with the term biologically compatible carrier or medium, refers to reagents, cells, compounds, materials, compositions, and/or dosage forms that are not only compatible with the cells and other agents to be administered therapeutically, but also are, within the scope of sound medical judgment, suitable for use in contact with the tissues of canines without excessive toxicity, irritation, allergic response, or other complication commensurate with a reasonable benefit/risk ratio. Pharmaceutically acceptable carriers suitable for use in the present invention include liquids, semi-solid (e.g., gels) and solid materials (e.g., cell scaffolds and matrices, tubes sheets and other such materials as known in the art and described in greater detail herein). These semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways.

An adjuvant, intends a biological agent capable of enhancing an immune response upon administration in a subject thereof. For examples of adjuvants, see Martin REMINGTON'S PHARM. SCI., 15th Ed. (Mack Publ. Co., Easton (1975) and Williams & Williams, (1995), and in the "PHYSICIAN'S DESK REFERENCE", $52^{nd}$ ed., Medical Economics, Montvale, N.J. (1998).

As used herein, the term OX40L (also known as OX40 ligand, CD134L, or TNRSF4) refers to a specific molecule associated with this name and any other molecules that have biological function as co-stimulatory molecules that share at least 80% amino acid sequence identity, preferably at least 90% sequence identity, more preferably at least 95% sequence identity and even more preferably at least 98% sequence identity with OX40L. The term "extracellular domain" refers to the portion of the protein that is located outside of the cell. Examples of the OX40L sequence are provided herein. In addition, the protein sequences associated with GenBank Accession Nos. AAA21871.1 (*Mus musculus*), AAC67236.1 (*Rattus norvegicus*), BAA20060.1 (*Oryctolagus cuniculus*), and ABB84240.1 (*Felis catus*) provide example sequences of OX40L in various animals. The sequences associated with each of the listed GenBank Accession Nos. are herein incorporated by reference in their entirety.

The term "canine" refers to canine animals. Examples include dogs and the like.

As used herein, the term "biological equivalent thereof" is used synonymously with "equivalent" unless otherwise specifically intended. When referring to a reference protein, polypeptide or nucleic acid, an equivalent intends those having minimal homology while still maintaining desired structure or functionality. Unless specifically recited herein, it is contemplated that any polynucleotide, polypeptide or protein mentioned herein also includes equivalents thereof. For example, an equivalent intends at least about 60%, or 65%, or 70%, or 75%, or 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid. Alternatively, a biological equivalent is a peptide encoded by a nucleic acid that hybridizes under stringent conditions to a nucleic acid or complement that encodes the peptide. Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

As used herein, the term "polynucleotide" refers to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, or EST), exons, introns, messenger RNA (mRNA), transfer RNA, ribosomal RNA, ribozymes, cDNA, RNAi, siRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching As used herein, the term "oligonucleotide" refers to a short polymer composed of deoxyribonucleotides, ribonucleotides or any combination thereof. Oligonucleotides are generally at least about 10, 15, 20, 25, 30, 40, 50, 60, 70, 80, 90, 100 or more nucleotides in length. An oligonucleotide may be used as a primer or as a probe.

The polynucleotides of this disclosure can be replicated using conventional recombinant techniques. Alternatively, the polynucleotides can be replicated using PCR technology. PCR is the subject matter of U.S. Pat. Nos. 4,683,195; 4,800,159; 4,754,065; and 4,683,202 and described in PCR: The Polymerase Chain Reaction (Mullis et al. eds, Birkhauser Press, Boston (1994)) and references cited therein. Yet further, one of skill in the art can use the sequences provided herein and a commercial DNA synthesizer to replicate the DNA. Accordingly, this disclosure also provides a process for obtaining the polynucleotides of this disclosure by providing the linear sequence of the polynucleotide, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can operatively link the polynucleotides to regulatory sequences for their expression in a host cell, described below. The polynucleotides and regulatory sequences are inserted into the host cell (prokaryotic or eukaryotic) for replication and amplification. The DNA so amplified can be isolated from the cell by methods well known to those of skill in the art. A process for obtaining polynucleotides by this method is further provided herein as well as the polynucleotides so obtained.

Also provided are host cells comprising one or more of the polypeptides or polynucleotides of this disclosure. In one aspect, the polypeptides are expressed and can be isolated from the host cells. In another aspect, the polypeptides are expressed and secreted. In yet another aspect, the polypeptides are expressed and present on the cell surface (extracellularly). Suitable cells containing the inventive polypeptides include prokaryotic and eukaryotic cells, which include, but are not limited to bacterial cells, algae cells, yeast cells, insect cells, plant cells, animal cells, mammalian cells, murine cells, rat cells, sheep cells, simian cells and human cells. A non-limiting example of algae cells is red alga *Griffithsia* sp. from which Griffithsin was isolated (Toshiyuki et al. (2005) J. Biol. Chem. 280(10):9345-53). A non-limiting example of plant cells is a *Nicotiana benthamiana* leaf cell from which Griffithsin can be produced in a large scale (O'Keefe (2009) Proc. Nat. Acad. Sci. USA 106(15):6099-6104). Examples of bacterial cells include *Escherichia coli* (Giomarelli et al. (2006), supra), *Salmonella* enteric, *Streptococcus gordonii* and *lactobacillus* (Liu et al. (2007) Cellular Microbiology 9:120-130; Rao et al. (2005) PNAS 102:11993-11998; Chang et al. (2003) PNAS 100(20):11672-11677; Liu et al. (2006) Antimicrob. Agents & Chemotherapy 50(10):3250-3259). The cells can be purchased from a commercial vendor such as the American Type Culture Collection (ATCC, Rockville Md., USA) or cultured from an isolate using methods known in the art. Examples of suitable eukaryotic cells include, but are not limited to 293T HEK cells, as well as the hamster cell line CHO, BHK-21; the murine cell lines designated NIH3T3, NS0, C127, the simian cell lines COS, Vero; and the human cell lines HeLa, PER.C6 (commercially available from Crucell) U-937 and Hep G2. A non-limiting example of insect cells include *Spodoptera frugiperda*. Examples of yeast useful for expression include, but are not limited to *Saccharomyces, Schizosaccharomyces, Hansenula, Candida, Torulopsis, Yarrowia*, or *Pichia*. See e.g., U.S. Pat. Nos. 4,812,405; 4,818,700; 4,929,555; 5,736,383; 5,955,349; 5,888,768 and 6,258,559.

A polynucleotide or polynucleotide region (or a polypeptide or polypeptide region) having a certain percentage (for example, about 60%, 65%, 70%, 75%, 80%, 85%, 90%, 95% or 97%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

An "equivalent" of a polynucleotide or polypeptide refers to a polynucleotide or a polypeptide having a substantial homology or identity to the reference polynucleotide or polypeptide. In one aspect, a "substantial homology" is greater than about 60%, 65%, 70%, 75%, 80%, 85%, 90%, 95% or 98% homology.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in an eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

Immunoglobulin "Fc" classically refers to the portion of the constant region generated by digestion with papain. It includes the lower hinge which has the interchain S—S bonds. The term "Fc" as used herein refers to a dimeric protein comprising a pair of immunoglobulin constant region polyeptides, each containing the lower part of the hinge, CH2 and CH3 domain. Such "Fc" fragment may or may not contain S—S interchain bridging in the hinge region. It should be understood that an Fc may be from any Ig class and, as such, may include a CH4 domain such as in the case of IgM. Mutant sequences of an Fc are known such as described by Wines. B. D. et al. (2000) J. Immunol. 164(10):5313-5318 and may be used herein. Proteins fused with immunoglobulin Fc are well known in the art for their therapeutic value. Examples include those described in Linderholm et al. *BioProcess International* 2014 November; 12 (10):20-27, which is herein incorporated by reference for all purposes.

"An effective amount" or "a therapeutically effective amount" refers to the amount of an active agent or a pharmaceutical composition sufficient to induce a desired biological and/or therapeutic result. That result can be alleviation of the signs, symptoms, or causes of a disease, or any other desired alteration of a biological system. The effective amount will vary depending upon the health condition or disease stage of the subject being treated, timing of administration, the manner of administration and the like, all of which can be determined readily by one of ordinary skill in the art. A therapeutically effective dose can be estimated initially from cell culture assays by determining an IC50. A dose can then be formulated in animal models to achieve a circulating plasma concentration range that includes the IC50 as determined in cell culture. Such information can be used to more accurately determine useful initial doses in humans. Levels of drug in plasma may be measured, for example, by HPLC. The exact formulation, route of administration and dosage can be chosen by the individual physician in view of the patient's condition.

As used herein, the terms "treating," "treatment," and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder.

As used herein, the term "ameliorating" includes systemic relief or amelioration of the symptoms associated with the pathology and/or a delay in onset of symptoms. Clinical and sub-clinical evidence of "ameliorating" will vary with the pathology, the subject and the treatment.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, injection, topical application, intrapentoneal, intravenous and by inhalation. An agent of the present invention can be administered for therapy by any suitable route of administration. It will also be appreciated that the preferred route will vary with the condition and age of the recipient, and the disease being treated.

As used herein, the term "vaccine" refers to a formulation comprising one or more biological agents capable of inducing an immune response upon administration in a subject thereof. Biological agents include but are not limited to cancer cell lysates or a cell therapy. Examples of vaccines include but are not limited to dendritic cell vaccines, peptide vaccines, tumor cell lysate vaccines, and vaccines that can be used as a therapy for cancer in canines Methods of preparation for cell lysate vaccines are well known in the art. In one embodiment, cells are collected and washed multiple times with PBS, re-suspended in PBS, and flash-frozen with liquid nitrogen. Cell lysis is induced by freezing in liquid nitrogen and thawing in a water bath. 65 µg of cell lysate are combined with 50 µg of CpG 1826, which can be purchased from Integrated DNA Technologies, or 10 µg of polyICLC, which can be purchased from Oncovir, Inc., in a 100 µL final volume to produce the final vaccines. See Murphy et al., "An in vivo immunotherapy screen of costimulatory molecules identifies Fc-OX40L as a potent reagent for the treatment of established murine gliomas." Clin Cancer Res 18 (17): 4657-4668, which is herein incorporated by reference for all purposes.

A dendritic cell vaccine is a recombinant dendritic cell that expresses a cancer or tumor antigen. It should be understood that the dendritic cell vaccine that is administered to the canine is relevant to the purpose of the therapy, e.g., a dendritic cell relevant to glioblastoma will be co-administered to treat glioblastoma, and not a lymphoma. Thus the dendritic cell vaccine is "cancer- or tumor-relevant."

The term "dendritic cell or cells" (DC) refers to a diverse population of morphologically similar cell types found in a variety of lymphoid and non-lymphoid tissues (Steinman, R. M. (1991) Ann. Rev. Immunol. 9:271-296). Dendritic cells constitute the most potent and preferred APCs in the organism. A subset, if not all, of dendritic cells are derived from bone marrow progenitor cells, circulate in small numbers in the peripheral blood and appear either as immature Langerhans' cells or terminally differentiated mature cells. While the dendritic cells can be differentiated from monocytes, they possess distinct phenotypes. For example, a particular differentiating marker, CD14 antigen, is not found in dendritic cells but is possessed by monocytes. Methods to generate dendritic cell vaccines are known in the art and incorporated herein, e.g., see WO 2014/090795 A1; EP 27365227 A; EP 274334 A1; WO 2002/044338; and U.S. Pat. No. 8,597,946.

Also, mature dendritic cells are not phagocytic, whereas the monocytes are strongly phagocytosing cells. It has been shown that DCs provide all the signals necessary for T cell activation and proliferation.

"Immune response" broadly refers to the antigen-specific responses of lymphocytes to foreign substances. Any substance that can elicit an immune response is said to be "immunogenic" and is referred to as an "immunogen". All immunogens are antigens, however, not all antigens are immunogenic. An immune response of this disclosure can be humoral (via antibody activity) or cell-mediated (via T cell activation).

As used herein, the term "human adiponectin signal peptide and the collagen-like domain of the human adiponectin protein" (ADP) is the short region of the human protein adiponectin that is responsible for targeting the protein for secretion outside the cell. ADP comprises a collagen-like domain. ADP facilitates the generation of an active trimer and hexamer of canina OX40L that is required for full biological activity and binding to the OX40 receptor in a canine.

The compositions and polypeptides of the present invention can be used in the manufacture of medicaments and for the treatment of veterinary animals by administration in accordance with conventional procedures, such as an active ingredient in pharmaceutical compositions.

The terms "cancer," "neoplasm," and "tumor," used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by such procedures as CAT scan, magnetic resonance imaging (MRI), X-ray, ultrasound or palpation. Biochemical or immunologic findings alone may be insufficient to meet this definition.

A neoplasm is an abnormal mass or colony of cells produced by a relatively autonomous new growth of tissue. Most neoplasms arise from the clonal expansion of a single cell that has undergone neoplastic transformation. The transformation of a normal to a neoplastic cell can be caused by a chemical, physical, or biological agent (or event) that directly and irreversibly alters the cell genome. Neoplastic cells are characterized by the loss of some specialized functions and the acquisition of new biological properties, foremost, the property of relatively autonomous (uncontrolled) growth. Neoplastic cells pass on their heritable biological characteristics to progeny cells.

The past, present, and future predicted biological behavior, or clinical course, of a neoplasm is further classified as benign or malignant, a distinction of great importance in diagnosis, treatment, and prognosis. A malignant neoplasm manifests a greater degree of autonomy, is capable of invasion and metastatic spread, may be resistant to treatment, and may cause death. A benign neoplasm has a lesser degree of autonomy, is usually not invasive, does not metastasize, and generally produces no great harm if treated adequately.

Cancer is a generic term for malignant neoplasms. Anaplasia is a characteristic property of cancer cells and denotes a lack of normal structural and functional characteristics (undifferentiation).

A tumor is literally a swelling of any type, such as an inflammatory or other swelling, but modern usage generally denotes a neoplasm. The suffix "-oma" means tumor and usually denotes a benign neoplasm, as in fibroma, lipoma, and so forth, but sometimes implies a malignant neoplasm, as with so-called melanoma, hepatoma, and seminoma, or even a non-neoplastic lesion, such as a hematoma, granuloma, or hamartoma. The suffix "-blastoma" denotes a neoplasm of embryonic cells, such as neuroblastoma of the adrenal or retinoblastoma of the eye.

Histogenesis is the origin of a tissue and is a method of classifying neoplasms on the basis of the tissue cell of origin. Adenomas are benign neoplasms of glandular epithelium. Carcinomas are malignant tumors of epithelium. Sarcomas are malignant tumors of mesenchymal tissues. One system to classify neoplasia utilizes biological (clinical) behavior, whether benign or malignant, and the histogenesis, the tissue or cell of origin of the neoplasm as determined by histologic and cytologic examination. Neoplasms may originate in almost any tissue containing cells capable of mitotic division. The histogenetic classification of neoplasms is based upon the tissue (or cell) of origin as determined by histologic and cytologic examination.

"Suppressing" tumor growth indicates a growth state that is curtailed compared to growth without any therapy. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth means any or all of the following states: slowing, delaying, and "suppressing" tumor growth indicates a growth state that is curtailed when stopping tumor growth, as well as tumor shrinkage.

The term "culturing" refers to the in vitro propagation of cells or organisms on or in media of various kinds. It is understood that the descendants of a cell grown in culture may not be completely identical (morphologically, genetically, or phenotypically) to the parent cell. By "expanded" is meant any proliferation or division of cells.

Modes for Carrying Out the Disclosure

Therapeutic Compositions

Aspects of the disclosure relate to an isolated recombinant polypeptide comprising, or alternatively consisting essentially of, or yet further consisting of, an immunoglobulin domain and a canine OX40L extracellular domain polypeptide, wherein the canine OX40L extracellular domain polypeptide comprises, or alternatively consists essentially of, or yet further consists of from about amino acid 447 to about amino acid 698 of a polypeptide of SEQ ID NO: 2 as shown in FIG. 3, or about amino acid 332 to about amino acid 464 of a polypeptide of SEQ ID NO: 3 as shown in FIG. 4, or a biological equivalent of each thereof. In one aspect the immunoglobulin domain is a mammalian immunoglobulin domain, e.g., human, canine, murine, simian, feline, or bovine. In one aspect, the immunoglobulin domain is a canine polypeptide. In one embodiment, the immunoglobulin domain is fused to the canine OX40L extracellular domain polypeptide, e.g., directly or indirectly (through a peptide linker (e.g., from 1 to about 10 amino acids, or other linker) covalently attached to each other. In another embodiment, the immunoglobulin domain comprises, or alternatively consists essentially of, or yet further consists of, from about amino acid 196 to about amino acid 446 of the polypeptide of SEQ ID NO: 2 as shown in FIG. 3, or about amino acid 106 to about amino acid 331 of the polypeptide of SEQ ID NO: 3 as shown in FIG. 4, or a biological equivalent of each thereof. In a specific embodiment, the immunoglobulin domain is a mammalian immunoglobulin Fc, e.g., human, feline or canine.

Without being bound by theory, the immunoglobulin Fc fused to the soluble OX40L polypeptide provides antibody effector functions such as binding by Fc receptor bearing cells or activation of serum complement. Such immunoglobulin Fc may be a human Ig Fc or a canine Ig Fc. The isolated canine OX40L extracellular domain polypeptide can be fused to an immunoglobulin (i.e., Fc region) by methods known in the art. For example, a nucleotide sequence comprising the OX40L polypeptide and Fc region can be cloned into an expression vector such as Glutamine Synthesis Gene Amplification System using expression vector pEE12 and transfected into the NS0 murine myeloma cell line. The expressed fusion protein can be purified by tandem protein-A affinity and ion-exchange chromatography.

The human OX40L is a type II membrane protein which contains 183 amino acids (no signal sequence). The human protein contains a cytoplasmic domain at residues 1-23, a transmembrane domain at residues 24-50 and an extracellular domain at residues 51-183. The nucleotide sequence of human OX40L (3510 bp, with the coding sequence being 157-708) is available in public databases (see Genbank accession no. NM_003326.2). The nucleotide sequence of canine OX40L (552 bp) is available in public databases (see Genbank accession No. XM_547459.1). OX40L is described by Godfry et al., J Exp Med. 1994 Aug. 1; 180(2):757-62. OX40L is expressed by dendritic cells and other APC and binds to OX40 which is present on activated T cells.

In a further embodiment, the canine OX40L extracellular domain polypeptide of the isolated recombinant polypeptide as described herein is fused to ADP. ADP facilitates the generation of an active trimer and hexamer of canine OX40L that is required for full biological activity and binding to the OX40 receptor in the canine. In a related embodiment, the ADP comprises, or alternatively consists essentially of, or yet further consists of, from about amino acid 1 to about amino acid 195 of the polypeptide of SEQ ID NO: 2 (FIG. 3), or about amino acid 1 to about amino acid 105 of the polypeptide of SEQ ID NO: 3 (FIG. 4), or a biological equivalent of each thereof.

The OX40L extracellular domain may be directly fused or indirectly fused through a linker to an immunoglobulin and/or ADP either through the amino terminal or carboxy terminal end. The decision to link to either the N or C terminus of the other protein depends on several factors, including ease of cloning and expression level. However, it is important that any choice substantially preserves the biological activity and/or function of each of the fused components.

In one embodiment, the carboxy terminus of the immunoglobulin domain is directly fused or indirectly fused through a linker to the amino terminus of the canine OX40L extracellular domain polypeptide. In another embodiment, the carboxy terminus of ADP is directly fused or indirectly fused to the amino terminus of the immunoglobular domain.

An additional aspect of the disclosure relates to an isolated recombinant polypeptide comprising SEQ ID NO: 2 as shown in FIG. 3, or SEQ ID NO: 3 as shown in FIG. 4, or a biological equivalent of each thereof. In another embodiment, provided herein is a recombinant polypeptide produced by expression of the polynucleotide of FIG. 2 in a suitable expression vector, and the polypeptide isolated from the expression system. An example of a suitable expression system is a vector and host cell for recombinant product of the polypeptide in a host system using methods known in the art. In a further aspect, the polypeptide and polynucleotides can further comprise, or alternatively consist essentially of, or yet further consist of a detectable label or other label for ease of use and isolation.

As used herein, the term "a detectable label" intends a directly or indirectly detectable compound or composition that is conjugated directly or indirectly to the composition to be detected, e.g., N-terminal histadine tags (N-His), magnetically active isotopes, e.g., $^{115}$Sn, $^{117}$Sn, and $^{119}$Sn, a non-radioactive isotopes such as $^{13}$C and $^{15}$N, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g., radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, luminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component.

Examples of luminescent labels that produce signals include, but are not limited to bioluminescence and chemiluminescence. Detectable luminescence response generally comprises a change in, or an occurrence of, a luminescence signal. Suitable methods and luminophores for luminescently labeling assay components are known in the art and described for example in Haugland, Richard P. (1996) Handbook of Fluorescent Probes and Research Chemicals ($6^{th}$ ed.). Examples of luminescent probes include, but are not limited to, aequorin and luciferases.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals ($6^{th}$ ed.).

A further aspect relates to a composition comprising, or alternatively consisting essentially of, or yet further consisting of:
a) an isolated recombinant polypeptide described herein; and
b) a pharmaceutically acceptable carrier.

In one embodiment, the composition comprising an isolated recombinant polypeptide described herein and a pharmaceutically acceptable carrier further comprises, or alternatively consists essentially of, or yet further consists of, a vaccine comprising a cancer cell lysate or a cell therapy.

The term "cell therapy" as used herein refers to isolation and administration of immune cells. In one embodiment, the immune cells are dendritic cells. Immune cells can also refer to T cells, B cells, helper T cells, cytotoxic T cells, natural killer cells, and the like. In one embodiment, the immune cells are autologous. In another embodiment the cells are allogeneic, and can be from a canine or other species. In another embodiment the immune cells are generated ex vivo. For example, dendritic cells may be prepared from myeloid or monocytoid precursor cells found in the peripheral blood or bone marrow. Lymphocytes such as B cells, T cells, and natural killer cells may be harvested from leucopheresis product from a donor. These and other methods for isolation and generation of immune cells are well known in the art. In some embodiments, the immune cells are pulsed with tumor immunogens (e.g., proteins, peptides, DNA/RNA, whole tumor cell, etc.). In some embodiments, the immune cells are genetically modified to produce a desired phenotype. Related embodiments include utilizing viral and non-viral vector-mediated transduction to produce the genetically modified immune cells.

Immune cells may be matured ex vivo or in situ. In some embodiments, activating cytokines and costimulatory molecules known in the art are used to enhance maturation of cells ex vivo. For example, to enhance dendritic cell maturation and activation, a "cocktail" of may include, among other components, cytokines such as IL4, GM-CSF and TNF-α, IL-6, IL-1β, prostaglandin E2 and/or costimulatory molecules such as CD80, CD86, CD40, and CD54 and/or toll-like-receptor agonists such as IFN γ, LPS, and PolyI:C. Similarly, natural killer cells may be activated ex vivo with cytokines IL-2 and IL-15. Antigen specific cytotoxic T cells can be activated trough repeated stimulation with APCs and relevant cytokines. Such maturation and activation are well-known in the art and can be performed through well-known procedures. See Okur, Fatma V., and Malcolm K. Brenner, "Cellular immunotherapy of cancer," Immunotherapy of Cancer. Humana Press, 2010. 319-345, which is herein incorporated by reference for all purposes.

In a further embodiment, the cell therapy may include adoptive transfer of immune cells to enhance anti-tumor immunity. As used herein "adoptive transfer" refers to the administration of immune cells, from another individual or from the same individual. These are preferably T cells, which may be activated ex vivo to enhance their ability to function in supporting an anti-tumor immune response. Adoptively transferred immune cells may be activated ex vivo by any of a variety of well-known agents including, for example, exposure to IL-2 and/or to anti-CD3 antibodies. Ex vivo activation also may include exposure to a cancer cell vaccine. Such cancer cell vaccine may constitute live (but non-replicating), or killed cancer cells from the individual to be treated or from another cancer entirely. The vaccine also may be a cancer cell extract or purified vaccine preparation derived from cancer cells. Cancer cell vaccines are well known in the art and may be prepared in accordance with well-known methods.

In one embodiment, the composition described herein further comprises, or alternatively consists essentially of, or yet further consists of an adjuvant. In one embodiment, the adjuvant is an oligonucleotide comprising, or alternatively consisting essentially of, or yet further consisting of one or more immunostimulatory sequence motifs, the motif comprising at least one unmethylated CG dinucleotide. As used herein, an "oliognucleotide comprising an immunostimulatory sequence motif which contains at least one unmethylated CG dinucleotide" includes sequences that bind to the TLR9 receptor on B cells and plasmacytoid dendritic cells (pDCs) and initiate an immunostimulatory response. Such response may include maturation, differentiation and/or proliferation of natural killer (NK) cells, T cells and monocytes/macrophages. Many such immunostimulatory sequence motifs are known and described in the art while others may be identified by routine efforts. Examples include those described in U.S. Patent Application Publication No. 2006/0135459, which is herein incorporated by reference for all purposes. An immunostimulatory sequence motif which contains at least one unmethylated CG dinucleotide refers to the portion of an oligonucleotide that includes the unmethylated CG dinucleotide and several nucleotides on each side of the CpG that are critical for the immunostimulatory activity. For example, the immunostimulatory motif containing the CG dinucleotide is shown bolded and italicized with the CpG bolded and underlined in the following sequence: 5'-TCGTCGTTT-3' (SEQ ID NO: 6).

Oligonucleotides which comprise an immunostimulatory sequence motif that contains at least one unmethylated CG dinucleotide have been referred to the in art as "oligodeoxynucleotide containing unmethylated CpG motifs," or "CpG oligodeoxynucleotides ("CpG ODNs"). The phrase "oliognucleotide comprising an immunostimulatory sequence motif which contains at least one unmethylated CG dinucleotide" may be referred to herein as a "CpG immunostimulatory oligonucleotide." Cells stimulated by CpG immunostimulatory oligonucleotide secrete cytokines and chemokines (IL-1, IL-6, IL-18 and TNF) including Th1-biased cyokines (interferon-.gamma., IFN-.gamma., and IL-12) to create a pro-inflammatory immune response (Klinman, Nature Rev. Immunol. (2004) 4:249-258). Also stimulated are professional antigen-presenting cells (APCs) which include macrophages and dendritic cells (Krieg et al., Nature (1995) 374:546-549; Klinman et al. PNAS (1996) 93:2879-2883).

The CpG ODN contain one or more unmethylated CG dinucleotides arranged within a specific sequence (Tokunaga et al. (1984) JNCI 72:955-962; Messina et al. (1991) J. Immunol. 147:1759-1764; Krieg et al. (1995) Nature 374: 546-549). The optimal CpG flanking region in mice consists of two 5' purines and two 3' pyrimidines, whereas the optimal motif in humans and certain other species is TCGTT (SEQ ID NO: 4) and/or TCGTA (SEQ ID NO: 5) (Klinman, D. M. (2004) Nature Rev. Immunol. 4:249-258). The CpG immunostimulatory oligonucleotide is generally from 6 to 100 nucleotides in length, more preferably between about 15 to 25 nucleotides in length. As described by Sen et al., (Cell Immunol. 2004 November-December; 232(1-2):64-74), portions of an oligonucleotide that has immunostimulatory motifs containing an unmethylated CpG can be replaced with RNA. For example, the RNA can be used in the oligonucleotide to flank the critical immunostimulatory motif.

The TLR9 receptor has been reported to diverge through evolution, so the precise sequence motifs (unmethylated CpG dinucleotides plus flanking regions) optimal for stimulating immune cells from different animal species varies (Klinman, D. M. (2004) Nature Rev. Immunol. 4:249-258). For example, the TLR9 molecules in mice differ from those in humans by 24% at the amino-acid level. It has been reported that the cell populations that express TLR9 have been reported to differ between species (Klinman, D. M. (2004) Nature Rev. Immunol. 4:249-258). In mice, immune cells of the myeloid lineage (including monocytes, macrophages and myeloid DCs) express TLR9 and respond to CpG stimulation, whereas in humans, these cell types generally do not express TLR9 and cannot be directly activated by CpG ODNs (Klinman, D. M. (2004) Nature Rev. Immunol. 4:249-258). The structural characteristics of human TLR9 are found in the Swiss-Prot database under accession no. Q9NR96. The molecule is synthesized as a 1032 amino acid precursor of which about 25 amino acids are removed as a leader sequence leaving a 1007 amino acid receptor.

In a further embodiment, the oligonucleotide contains multiple immunostimulatory sequence motifs. In yet further embodiments, the immunostimulatory sequence motif of the oligonucleotide comprises, or alternatively consists essentially of, or yet further consists of TCGTT (SEQ ID NO: 4), TCGTA (SEQ ID NO: 5), or both.

A further aspect of the disclosure relates to an isolated polynucleotide encoding the isolated recombinant polypeptide described herein. Related embodiments include vector and/or host cells comprising the isolated polynucleotide encoding the isolated recombinant polypeptide described herein. Suitable vectors include mammalian expression vectors, viral vectors, retroviral vectors, bacterial vectors, or non-viral vectors such as liposomes, and the like. Host cells suitable for replicating and for supporting recombinant expression of protein are well known in the art. Such cells may be transfected or transduced as appropriate with the particular expression vector and large quantities of vector containing cells can be grown for seeding large scale fermenters to obtain sufficient quantities of the protein for clinical applications. Host cells can be a prokaryotic or eukaryotic cell, such as a bacteria, such as *E. coli*, a yeast, a mammalian cell such as a canine cell, a human cell, a simian cell, a murine cell, a Chinese hamster ovary cell (CHO), insect cells, or the like. Standard technologies are known in the art to express foreign genes in these systems.

Other related embodiments include compositions comprising, or alternatively consisting essentially of, or yet further consisting of the vector and/or host cell as described herein.

Also provided is a method for preparing a therapeutic polypeptide, comprising, or alternatively consisting essentially of, or yet further consisting of expressing the isolated polynucleotide (as shown in FIG. 2) described herein in a suitable expression system. In general, nucleic acid encoding the protein can be cloned into an expression vector for high yield expression of the encoded product. The expression vector can be part of a plasmid, virus, or may be a nucleic acid fragment. The expression vector includes an expression cassette into which the nucleic acid encoding the protein is cloned in operable association with a promoter and optionally an enhancer. The expression cassette may also include other features such as an origin of replication, and/or chromosome integration elements such as retroviral LTRs, or adeno associated viral (AAV) ITRs. If secretion of the protein is desired, DNA encoding a signal sequence may be placed upstream of the nucleic acid encoding the mature amino acids of the protein. DNA encoding a short protein sequence that could be used to facilitate later purification (e.g., a histidine tag) or assist in labeling the protein may be included within or at the ends of the protein encoding nucleic acid. In a related embodiment, the method further comprises separating or purifying the polypeptide from the expression system.

Method aspects of the disclosure relate to methods for treating or ameliorating the symptoms of cancer in a canine comprising, or alternatively consisting essentially of, or yet further consisting of administering to the canine in need thereof an effective amount of the isolated recombinant polypeptide described herein, thereby treating the cancer.

In one embodiment, the method further comprises, or alternatively consists essentially of, or yet further consists of administering to the canine in need thereof an effective amount of the compositions described herein. In one embodiment, the composition comprises, or alternatively consists essentially of, or yet further consists of a) an isolated recombinant polypeptide described herein; and b) a pharmaceutically acceptable carrier. In another embodiment, the composition further comprises, or alternatively consists essentially of, or yet further consists of a vaccine comprising a cancer cell lysate or a cell therapy. In a further embodiment, the composition yet further comprises, or alternatively consists essentially of, or yet further consists of an adjuvant. In one embodiment, an adjuvant is an oligonucleotide comprising one or more immunostimulatory sequence motifs, the motif comprising at least one unmethylated CG dinucleotide. In another embodiment, the oligonucleotide contains multiple immunostimulatory sequence motifs. In a further embodiment, the immunostimulatory sequence motif comprises one or both of SEQ ID NO: 4 or SEQ ID NO: 5.

In further embodiments, the compositions and methods described herein yet further comprises, or alternatively consists essentially of, or yet further consists of administering to the canine an effective amount of a tumor suppressive therapy. Examples of tumor suppressive therapies are described herein.

Therapeutic Compositions

Cancers treatable using the methods of the disclosure include carcinomas, sarcomas, leukemias, lymphomas and other types of cancer. Carcinomas include those of lung, breast, colon, ovarian, prostate, and the like. These cancers may be primary or metastatic. In the case of leukemias and lymphomas, the cancer cells treatable with the invention methods include those in the form of a solid tumor as well as cancer cells in the bone marrow and in the circulation.

In certain embodiments, the cancer is a solid tumor. In a further embodiment, the tumor is a tumor of the group glioblastoma, lung, renal, gastrointestinal, melanoma, sarcoma, breast, leukemia, lymphoma, and carcinoma. In a specific embodiment, the tumor is a glioblastoma.

In one embodiment, the isolated recombinant polypeptide and the vaccine may be administered simultaneously or sequentially or both. The administration may take place over a period of days, or weeks, or months. The isolated recombinant polypeptide may be administered in the same composition or in different compositions, at the same frequency or at different frequencies. In a further embodiment, the isolated recombinant polypeptide and the vaccine are administered after surgical resection of a solid tumor.

In one embodiment, the isolated recombinant polypeptide and the tumor suppressive therapy may be administered simultaneously or sequentially or both. The administration may take place over a period of days, or weeks, or months. The isolated recombinant polypeptide may be administered in the same composition or in different compositions, at the same frequency or at different frequencies. In a further embodiment, the isolated recombinant polypeptide and the tumor suppressive therapy are administered after surgical resection of a solid tumor.

In a further embodiment, the tumor suppressive therapy and/or the vaccine and/or cell therapy are cancer- or tumor-relevant. As used herein, "cancer- or tumor-relevant therapy" is any treatment of a cancer or an associated condition/disorder in a cancer that includes stopping or suppressing and/or relieving the development of clinical symptoms of the cancer or an associated condition/disorder. In a specific embodiment where the solid tumor is glioblastoma, the cancer-relevant therapy is temozolamide (TMZ). TMZ is a conventional chemotherapeutic DNA-alkylating agent that is well known in the art for its cytoxicity on tumor cells, especially those of brain cancer. It has been shown that the cytotoxic effect of TMZ is increased when it is administered with perillyl alcohol or an analogue thereof. See U.S. Pat. No. 8,236,862, which is herein incorporated by reference for all purposes.

Another aspect of the disclosure relates to a method for enhancing a therapy comprising a tumor suppressive therapy in a canine in need thereof, comprising or alternatively consisting essentially of, or yet further consisting of administering an effective amount of the isolated recombinant polypeptide described herein and/or the composition described herein, to the canine having previously been administered the tumor suppressive therapy.

A further aspect of the disclosure relates to a kit comprising, or alternatively consisting essentially of, or yet further comprising the composition described herein and instructions for use.

Polypeptides and compositions described herein can be administered as a pharmaceutical or medicament formulated with a pharmaceutically acceptable carrier. Pharmaceutical compositions of the disclosure may be formulated as solutions or lyophilized powders for parenteral administration. Powders may be reconstituted by addition of a suitable diluent or other pharmaceutically acceptable carrier prior to use. Liquid formulations may be buffered, isotonic, aqueous solutions. Powders also may be sprayed in dry form. Examples of suitable diluents are normal isotonic saline solution, standard 5% dextrose in water, or buffered sodium or ammonium acetate solution. Such formulations are especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride, sodium citrate, and the like.

Alternately, compositions may be encapsulated, tableted or prepared in an emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation may be in the form of a syrup, elixir, emulsion, or an aqueous or non-aqueous suspension. For rectal administration, the invention compositions may be combined with excipients such as cocoa butter, glycerin, gelatin or polyethylene glycols and molded into a suppository.

Compositions may be formulated to include other medically useful drugs or biological agents. The compositions also may be administered in conjunction with the administration of other drugs or biological agents useful for the disease or condition to which the compositions of the disclosure are directed.

Tumor Suppressive Agents

In one specific embodiment, the composition comprises, or alternatively consists essentially of, or yet further consists of an effective amount of a tumor suppressive agent or therapy such as a therapeutic agent. Suitable therapeutic agents include, but are not limited to chemotherapeutic compounds such as DNA alkylating agents, topoisomerase inhibitors, endoplasmic reticulum stress inducing agents, a platinum compound, an antimetabolite, vincalkaloids, taxanes, epothilones, enzyme inhibitors, receptor antagonists, therapeutic antibodies, tyrosine kinase inhibitors, antibiotics, boron radiosensitizers (i.e., velcade) and chemotherapeutic combination therapies. Non-limiting examples of chemotherapeutic agents and therapeutic agents are provided here. Chemical and biological equivalents of these agents are within the scope of this disclosure.

In one aspect of the disclosure, the anticancer drug is a DNA alkylating agent which attaches an alkyl group to DNA. Such agents are well known in the art and are used to treat a variety of tumors. Non-limiting examples of a DNA alkylating agents are Nitrogen mustards, such as Mechlorethamine, Cyclophosphamide (Ifosfamide, Trofosfamide), Chlorambucil (Melphalan, Prednimustine), Bendamustine, Uramustine and Estramustine; Nitrosoureas, such as Carmustine (BCNU), Lomustine (Semustine), Fotemustine, Nimustine, Ranimustine and Streptozocin; Alkyl sulfonates, such as Busulfan (Mannosulfan, Treosulfan); Aziridines, such as Carboquone, ThioTEPA, Triaziquone, Triethylenemelamine; Hydrazines (Procarbazine); Triazenes such as Dacarbazine and Temozolomide; Altretamine and Mitobronitol.

In another aspect of the disclosure, the anticancer drug is a platinum based compound which is a subclass of DNA alkylating agents. Such agents are well known in the art and are used to treat a variety of cancers, such as, lung cancers, head and neck cancers, ovarian cancers, colorectal cancer and prostate cancer. Non-limiting examples of such agents include Carboplatin, Cisplatin, Nedaplatin, Oxaliplatin, Triplatin tetranitrate, Satraplatin, Aroplatin, Lobaplatin, and JM-216. (see McKeage et al. (1997) J. Clin. Oncol. 201:1232-1237 and in general, CHEMOTHERAPY FOR GYNECOLOGICAL NEOPLASM, CURRENT THERAPY AND NOVEL APPROACHES, in the Series Basic and Clinical Oncology, Angioli et al. Eds., 2004).

"Oxaliplatin" (Eloxatin®) is a platinum-based chemotherapeutic drug in the same family as cisplatin and carboplatin. It is typically administered in combination with fluorouracil and leucovorin in a combination known as FOLFOX for the treatment of colorectal cancer. Compared to cisplatin the two amine groups are replaced by cyclohexyldiamine for improved antitumour activity. The chlorine ligands are replaced by the oxalato bidentate derived from oxalic acid in order to improve water solubility. Equivalents to Oxaliplatin are known in the art and include without limitation cisplatin, carboplatin, aroplatin, lobaplatin, nedaplatin, and JM-216 (see McKeage et al. (1997) J. Clin. Oncol. 201:1232-1237 and in general, CHEMOTHERAPY FOR GYNECOLOGICAL NEOPLASM, CURRENT THERAPY AND NOVEL APPROACHES, in the Series Basic and Clinical Oncology, Angioli et al. Eds., 2004).

In one aspect of the disclosure, the anticancer drug is a topoisomerase inhibitor which is an agent that interferes with the action of topoisomerase enzymes (topoisomerase I and II). Topoisomerases are enzymes that control the changes in DNA structure by catalyzing the breaking and rejoining of the phosphodiester backbone of DNA. Such agents are well known in the art. Non-limiting examples of Topoisomerase I inhibitors include Campothecine derivatives including CPT-11/Irinotecan, SN-38, APC, NPC, camptothecin, topotecan, exatecan mesylate, 9-nitrocamptothecin, 9-aminocamptothecin, lurtotecan, rubitecan, silatecan, gimatecan, diflomotecan, extatecan, BN-80927, DX-8951f, and MAG-CPT as described in Pommier (2006) Nat. Rev. Cancer 6(10):789-802 and U.S. Patent Appl. No. 2005/0250854; Protoberberine alkaloids and derivatives thereof including berrubine and coralyne as described in Li et al. (2000) Biochemistry 39(24):7107-7116 and Gatto et al. (1996) Cancer Res. 15(12):2795-2800; Phenanthroline derivatives including Benzo[i]phenanthridine, Nitidine, and fagaronine as described in Makhey et al. (2003) Bioorg. Med. Chem. 11 (8):1809-1820; Terbenzimidazole and derivatives thereof as described in Xu (1998) Biochemistry 37(10):3558-3566; and Anthracycline derivatives including Doxorubicin, Daunorubicin, and Mitoxantrone as described in Foglesong et al. (1992) Cancer Chemother. Pharmacol. 30(2):123-125, Crow et al. (1994) J. Med. Chem. 37(19): 3191-3194, and (Crespi et al. (1986) Biochem. Biophys. Res. Commun. 136(2):521-8.

In one aspect of the disclosure, the topoisomerase I inhibitors can be selected from the group of, but not limited to, Campothecine derivatives including CPT-11/Irinotecan, SN-38, APC, NPC, camptothecin, topotecan, exatecan mesylate, 9-nitrocamptothecin, 9-aminocamptothecin, lurtotecan, rubitecan, silatecan, gimatecan, diflomotecan, extatecan, BN-80927, DX-8951f, and MAG-CPT as described in Pommier (2006) Nat. Rev. Cancer 6(10):789-802 and U.S. Patent Application Publication No. 2005/0250854; Protoberberine alkaloids and derivatives thereof including berrubine and coralyne as described in Li et al. (2000) Biochemistry 39(24):7107-7116 and Gatto et al. (1996) Cancer Res. 15(12):2795-2800; Phenanthroline derivatives including Benzo[i]phenanthridine, Nitidine, and fagaronine as described in Makhey et al. (2003) Bioorg. Med. Chem. 11(8):1809-1820; Terbenzimidazole and derivatives thereof as described in Xu (1998) Biochemistry 37(10):3558-3566; and Anthracycline derivatives including Doxorubicin, Daunorubicin, and Mitoxantrone as described in Foglesong et al. (1992) Cancer Chemother. Pharmacol. 30(2):123-125, Crow et al. (1994) J. Med. Chem. 37(19):3191-3194, and (Crespi et al. (1986) Biochem. Biophys. Res. Commun. 136(2):521-8, will be used in combination therapy with antibody based chemotherapy described above to treat patients identified with the appropriate genetic markers.

Irinotecan (CPT-11) is sold under the tradename of Camptosar®. It is a semi-synthetic analogue of the alkaloid camptothecin, which is activated by hydrolysis to SN-38 and targets topoisomerase I. Chemical equivalents are those that inhibit the interaction of topoisomerase I and DNA to form a catalytically active topoisomerase I-DNA complex. Chemical equivalents inhibit cell cycle progression at G2-M phase resulting in the disruption of cell proliferation.

In another aspect, some agents inhibit Topoisomerase II and have DNA intercalation activity such as, but not limited to, Anthracyclines (Aclarubicin, Daunorubicin, Doxorubicin, Epirubicin, Idarubicin, Amrubicin, Pirarubicin, Valrubicin, Zorubicin) and Antracenediones (Mitoxantrone and Pixantrone).

In one aspect of the disclosure, Topoisomerase II inhibitors include, but are not limited to Etoposide and Teniposide.

In another aspect of the disclosure, dual topoisomerase I and II inhibitors selected from the group of, but not limited to, Saintopin and other Naphthecenediones, DACA and other Acridine-4-Carboxamindes, Intoplicine and other Benzopyridoindoles, TAS-103 and other 7H-indeno[2,1-c]Quinoline-7-ones, Pyrazoloacridine, XR 11576 and other Benzophenazines, XR 5944 and other Dimeric compounds, and Anthracenyl-amino Acid Conjugates as described in Denny and Baguley (2003) Curr. Top. Med. Chem. 3(3):339-353. In one aspect, they can be used in combination therapy with antibody based chemotherapy described above to treat patients identified with the appropriate genetic markers.

"Lapatinib" (Tykerb®) is an oncolytic dual EGFR and erbB-2 inhibitor. Lapatinib has been investigated as an anticancer monotherapy, as well as in combination with trastuzumab, capecitabine, letrozole, paclitaxel and FOLFIRI (irinotecan, 5-fluorouracil and leucovorin), in a number of clinical trials. It is currently in phase III testing for the oral treatment of metastatic breast, head and neck, lung, gastric, renal and bladder cancer.

A chemical equivalent of lapatinib is a small molecule or compound that is a tyrosine kinase inhibitor or alternatively a HER-1 inhibitor or a HER-2 inhibitor. Several TKIs have been found to have effective antitumor activity and have been approved or are in clinical trials. Examples of such include, but are not limited to Zactima (ZD6474), Iressa (gefitinib) and Tarceva (erlotinib), imatinib mesylate (STI571; Gleevec), erlotinib (OSI-1774; Tarceva), canertinib (CI 1033), semaxinib (SU5416), vatalanib (PTK787/ZK222584), sorafenib (BAY 43-9006), sutent (SU11248) and leflunomide (SU101).

A biological equivalent of lapatinib is a peptide, antibody or antibody derivative thereof that is a HER-1 inhibitor and/or a HER-2 inhibitor. Examples of such include but are not limited to the humanized antibody trastuzumab and Herceptin.

In one aspect of the disclosure, the therapeutic agent is an endoplasmic reticulum stress inducing agent. Examples of such agents include, but are not limited to, Celecoxib, dimethyl-celecoxib and boron radiosensitizers (i.e., valcade (Bortezomib)).

In another aspect of the disclosure, the anticancer drug is an antimetabolite agent which inhibits the use of a metabolite, i.e., another chemical that is part of normal metabolism. In cancer treatment, antimetabolites interfere with DNA production, thus cell division and growth of the tumor. Non-limiting examples of these agents are Folic acid based, i.e., dihydrofolate reductase inhibitors, such as Aminopterin, Methotrexate and Pemetrexed; thymidylate synthase inhibitors, such as Raltitrexed, Pemetrexed; Purine based, i.e., an adenosine deaminase inhibitor, such as Pentostatin, a thiopurine, such as Thioguanine and Mercaptopurine, a halogenated/ribonucleotide reductase inhibitor, such as Cladribine, Clofarabine, Fludarabine, or a guanine/guanosine: thiopurine, such as Thioguanine; or Pyrimidine based, i.e., cytosine/cytidine: hypomethylating agent, such as Azacitidine and Decitabine, a DNA polymerase inhibitor, such as Cytarabine, a ribonucleotide reductase inhibitor, such as Gemcitabine, or a thymine/thymidine: thymidylate synthase inhibitor, such as a Fluorouracil (5-FU).

Fluorouracil (5-FU) belongs to the family of therapy drugs called pyrimidine based anti-metabolites. 5-FU is transformed into different cytotoxic metabolites that are then incorporated into DNA and RNA thereby inducing cell cycle arrest and apoptosis. It is a pyrimidine analog, which is transformed into different cytotoxic metabolites that are then incorporated into DNA and RNA thereby inducing cell cycle arrest and apoptosis. Chemical equivalents are pyrimidine analogs which result in disruption of DNA replication. Chemical equivalents inhibit cell cycle progression at S phase resulting in the disruption of cell cycle and consequently apoptosis. Equivalents to 5-FU include prodrugs, analogs and derivative thereof such as 5'-deoxy-5-fluorouridine (doxifluoroidine), 1-tetrahydrofuranyl-5-fluorouracil (ftorafur), Capecitabine (Xeloda), S-1 (MBMS-247616, consisting of tegafur and two modulators, a 5-chloro-2,4-dihydroxypyridine and potassium oxonate), ralititrexed (tomudex), nolatrexed (Thymitaq, AG337), LY231514 and ZD9331, as described for example in Papamicheal (1999) The Oncologist 4:478-487.

Capecitabine and Tegafur are examples of chemical equivalents of 5-FU. It is a prodrug of (5-FU) that is converted to its active form by the tumor-specific enzyme PynPase following a pathway of three enzymatic steps and two intermediary metabolites, 5'-deoxy-5-fluorocytidine (5'-DFCR) and 5'-deoxy-5-fluorouridine (5'-DFUR). Capecitabine is marketed by Roche under the trade name Xeloda®.

Leucovorin (Folinic acid) is an adjuvant used in cancer therapy. It is used in synergistic combination with 5-FU to improve efficacy of the chemotherapeutic agent. Without being bound by theory, addition of Leucovorin is believed to enhance efficacy of 5-FU by inhibiting thymidylate synthase. It has been used as an antidote to protect normal cells from high doses of the anticancer drug methotrexate and to increase the antitumor effects of fluorouracil (5-FU) and tegafur-uracil. It is also known as citrovorum factor and Wellcovorin. This compound has the chemical designation of L-Glutamic acid N[4[[(2-amino-5-formyl1,4,5,6,7,8hexahydro4oxo6-pteridinyl)methyl]amino]benzoyl], calcium salt (1:1).

Examples of vincalkaloids, include, but are not limited to vinblastine, Vincristine, Vinflunine, Vindesine and Vinorelbine.

Examples of taxanes include, but are not limited to docetaxel, Larotaxel, Ortataxel, Paclitaxel and Tesetaxel. An example of an epothilone is iabepilone.

Examples of enzyme inhibitors include, but are not limited to farnesyltransferase inhibitors (Tipifarnib); CDK inhibitor (Alvocidib, Seliciclib); Proteasome inhibitor (Bortezomib); Phosphodiesterase inhibitor (Anagrelide); IMP dehydrogenase inhibitor (Tiazofurine); and Lipoxygenase inhibitor (Masoprocol).

Examples of tyrosine kinase inhibitors include, but are not limited to ErbB: HER1/EGFR (Erlotinib, Gefitinib, Lapatinib, Vandetanib, Sunitinib, Neratinib); HER2/neu (Lapatinib, Neratinib); RTK class III: C-kit (Axitinib, Sunitinib, Sorafenib); FLT3 (Lestaurtinib); PDGFR (Axitinib, Sunitinib, Sorafenib); and VEGFR (Vandetanib, Semaxanib, Cediranib, Axitinib, Sorafenib); bcr-abl (Imatinib, Nilotinib, Dasatinib); Src (Bosutinib) and Janus kinase 2 (Lestaurtinib).

PTK/ZK is a "small" molecule tyrosine kinase inhibitor with broad specificity that targets all VEGF receptors (VEGFR), the platelet-derived growth factor (PDGF) receptor, c-KIT and c-Fms. Drevs (2003) Idrugs 6(8):787-794. PTK/ZK is a targeted drug that blocks angiogenesis and lymphangiogenesis by inhibiting the activity of all known receptors that bind VEGF including VEGFR-1 (Flt-1), VEGFR-2 (KDR/Flk-1) and VEGFR-3 (Flt-4). The chemical names of PTK/ZK are 1-[4-Chloroanilino]-4-[4-pyridylmethyl]phthalazine Succinate or 1-Phthalazinamine, N-(4-chlorophenyl)-4-(4-pyridinylmethyl)-, butanedioate (1:1). Synonyms and analogs of PTK/ZK are known as Vatalanib, CGP79787D, PTK787/ZK 222584, CGP-79787, DE-00268, PTK-787, PTK-787A, VEGFR-TK inhibitor, ZK 222584 and ZK.

Examples of antibiotics include, but are not limited to actinomycin, Bleomycin, Mitomycin, Plicamycin.

Examples of receptor antagonists include, but are not limited to ERA (Atrasentan); retinoid X receptor (Bexarotene); and a sex steroid (Testolactone).

Examples of chemotherapeutic agents and combination therapies include, but are not limited to amsacrine, Trabectedin, retinoids (Alitretinoin, Tretinoin), Arsenic trioxide, asparagine depleter (Asparaginase/Pegaspargase), Celecoxib, Demecolcine, Elesclomol, Elsamitrucin, Etoglucid, Lonidamine, Lucanthone, Mitoguazone, Mitotane, Oblimersen, Temsirolimus, and Vorinostat.

"FOLFOX" is an abbreviation for a type of combination therapy that is used to treat colorectal cancer. It includes 5-FU, oxaliplatin and leucovorin. Information regarding this treatment is available on the National Cancer Institute's web site, cancer.gov, last accessed on Jan. 16, 2008.

"FOLFOX/BV" is an abbreviation for a type of combination therapy that is used to treat colorectal cancer. This therapy includes 5-FU, oxaliplatin, leucovorin and Bevacizumab. Furthermore, "XELOX/BV" is another combination therapy used to treat colorectal cancer, which includes the prodrug to 5-FU, known as Capecitabine (Xeloda) in combination with oxaliplatin and bevacizumab. Information regarding these treatments are available on the National Cancer Institute's web site, cancer.gov or from the National Comprehensive Cancer Network's web site, nccn.org, last accessed on May 27, 2008.

Examples of therapeutic antibodies include, but are not limited to anti-HER1/EGFR (Cetuximab, Panitumumab); Anti-HER2/neu (erbB2) receptor (Trastuzumab); Anti-EpCAM (Catumaxomab, Edrecolomab) Anti-VEGF-A (Bevacizumab); Anti-CD20 (Rituximab, Tositumomab, Ibritumomab); Anti-CD52 (Alemtuzumab); and Anti-CD33 (Gemtuzumab), as well as biological equivalents thereof.

Bevacizumab is sold under the trade name Avastin by Genentech. It is a humanized monoclonal antibody that binds to and inhibits the biologic activity of human vascular endothelial growth factor (VEGF). Biological equivalent antibodies are identified herein as modified antibodies and those which bind to the same epitope of the antigen, prevent the interaction of VEGF to its receptors (Flt01, KDR a.k.a. VEGFR2) and produce a substantially equivalent response, e.g., the blocking of endothelial cell proliferation and angiogenesis.

In one aspect, the "chemical equivalent" means the ability of the chemical to selectively interact with its target protein, DNA, RNA or fragment thereof as measured by the inactivation of the target protein, incorporation of the chemical into the DNA or RNA or other suitable methods. Chemical equivalents include, but are not limited to, those agents with the same or similar biological activity and include, without limitation a pharmaceutically acceptable salt or mixtures thereof that interact with and/or inactivate the same target protein, DNA, or RNA as the reference chemical.

In one aspect, the "biological equivalent" means the ability of the antibody to selectively bind its epitope protein or fragment thereof as measured by ELISA or other suitable methods. Biologically equivalent antibodies include, but are not limited to, those antibodies, peptides, antibody fragments, antibody variant, antibody derivative and antibody mimetics that bind to the same epitope as the reference antibody. An example of an equivalent Bevacizumab antibody is one which binds to and inhibits the biologic activity of human vascular endothelial growth factor (VEGF).

Formulations

The pharmaceutical compositions can be administered by any one of the following routes: ocular, oral, systemic (e.g., transdermal, intranasal or by suppository), or parenteral (e.g., intramuscular, intravenous or subcutaneous) administration. In some embodiments, the manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another manner for administering compounds of described herein is inhalation.

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI), mouth mask and dry powder inhalers (DPI). Nebulizer devices produce a stream of high velocity air that causes the therapeutic agents (which are formulated in a liquid form) to spray as a mist that is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI can dispense therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

For ocular administration, the compositions described herein can be formulated as a solution, emulsion, suspension, etc., suitable for administration to the eye. A variety of vehicles suitable for administering compounds to the eye are known in the art. Specific non-limiting examples are described in U.S. Pat. No. 6,261,547; U.S. Pat. No. 6,197,934; U.S. Pat. No. 6,056,950; U.S. Pat. No. 5,800,807; U.S. Pat. No. 5,776,445; U.S. Pat. No. 5,698,219; U.S. Pat. No. 5,521,222; U.S. Pat. No. 5,403,841; U.S. Pat. No. 5,077,033; U.S. Pat. No. 4,882,150; and U.S. Pat. No. 4,738,851.

The compositions can additional contain solid pharmaceutical excipients such as starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, particularly for injectable solutions, include water, saline, aqueous dextrose, and glycols.

Compressed gases may be used to disperse a composition described herein in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the composition in a formulation can vary within the full range employed by those skilled in the art. Typically, the formulation will contain, on a volume percent (v/v %) basis, from about 0.01-99.99 v/v % of a composition described herein based on the total formulation, with the balance being one or more suitable pharmaceutical excipients. In some embodiments, the composition is present at a level of about 1-80 v/v %.

Thus, the composition of this disclosure can be formulated for administration intranasally as a spray or in a drop; transdermally via a transdermal patch or iontorphoresis and by inhalation using a nebulizer, MDI or similar device. As such, the compositions can further comprise, or alternatively consist essentially of, or yet further consist of, a permeation or penetration enhancer, a plasticizer, or the like making the composition suitable for transdermal administration. In one aspect, the disclosure relates to a transdermal reservoir having within it an effective amount of a composition of this invention for transdermal administration of the composition. In a further aspect, the invention provides a transdermal device containing the transdermal reservoir. The transdermal reservoir and/or device can be used to administer an effective amount of the composition of this disclosure to a subject in need of treatment. These devices are suitable to administer pain medications such as analgesics and narcotics. Examples of these therapeutic agents are provided supra.

This disclosure also provides the compositions as described above for intranasal administration. As such, the compositions can further comprise, or alternatively consist essentially of, or yet further consist of, a permeation or penetration enhancer or the like making the composition suitable for intranasal administration. In one aspect, the disclosure relates to an intranasal formulation having within it an effective amount of a composition described herein for intranasal administration of the composition. These formulations are suitable to cancer drugs or drugs to treat neurological disorders. Examples of these drugs are provided below.

This disclosure also provides the compositions as described above for administration by inhalation. As such, the compositions can further comprise, or alternatively consist essentially of, or yet further consist of, a permeation or penetration enhancer or the like making the composition suitable for administration by inhalation. In one aspect, the disclosure relates to a formulation for administration by inhalation having within it an effective amount of a composition described herein for inhalation of the composition. These formulations are suitable to administer cancer drugs or drugs to treat neurological disorders. Examples of these drugs are provided supra.

The following examples serve to illustrate the present disclosure. These examples are in no way intended to limit the scope of the invention.

EXAMPLES

Example 1. Canine OX40L Fusion Protein for the Immunotherapy of Tumors of the Dog OX40 is a co-stimulatory receptor expressed on CD4 and CD8 T cells that promotes survival, proliferation, and generation of memory while simultaneously inhibiting the suppressive function of regulatory T cells (Gough, M. J. et al. (2008) Cancer Res. 68:5206-5215; Piconese, S. et al. (2009) J. Exp. Med. 205:825-839; Ishii, N. et al. (2007) Blood 110:2501-2510). OX40 agonist antibodies are currently in clinical trials for the treatment of a variety of cancers (Weinberg, A. D. et al. (2006) J. Immunother. 29:575-585). This example demonstrates that the addition of Fc-mOX40L fusion protein (Sadun, R. E. et al. (2008) J. Immunother. 31:235-245) to vaccine protocol developed by Applicant dramatically increased overall survival and cure rates (FIG. 1A). Using bioluminescence imaging, mice treated by the combination of vaccination (dendritic cell vaccine or cell therapy) and Fc-mOX40L exhibited complete resolution of established tumors (FIG. 1B).

Figure 1C:
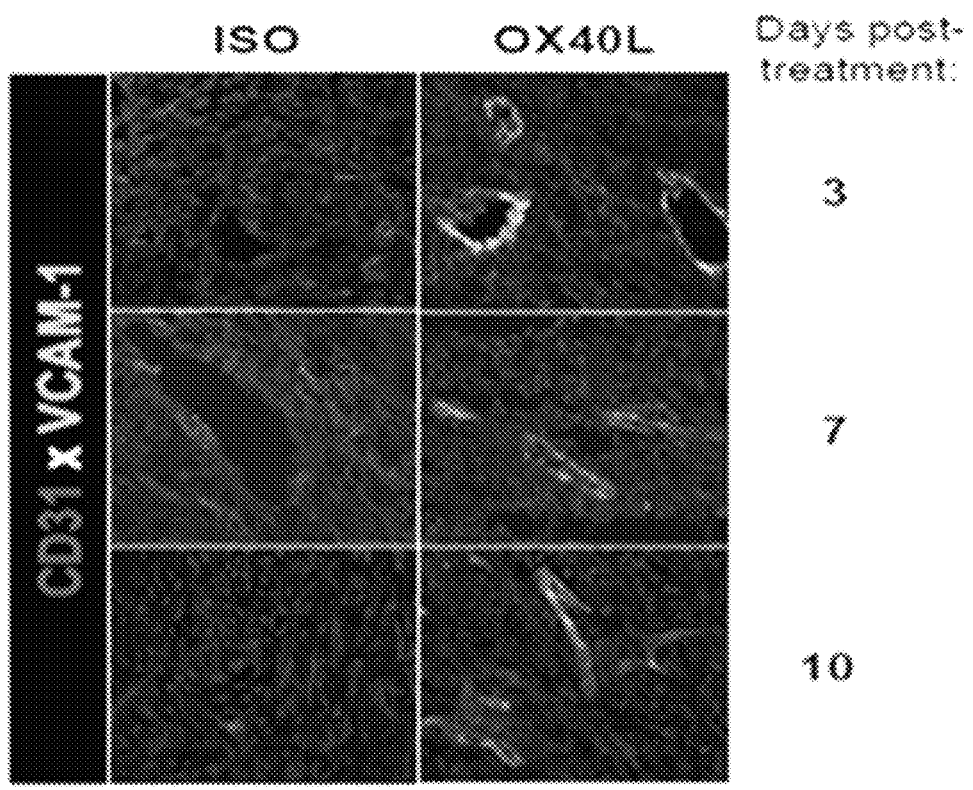

Moreover, mechanistic studies using Fc-mOX40L showed that this reagent provided missing co-stimulation and changed the tumor microenvironment by up-regulating adhesion molecules in the tumor vasculature to enable infiltration of immune cells capable of killing the tumor (Pardee, A. D. (2010) Cancer Res. 70:9041-9052) (FIG. 1C).

Based upon these impressive results in the mouse, additional clinical studies were planned in the dog requiring the generation of a canine compatible reagent described below. In this disclosure, a canine homotrimer reagent, designated ADP-Fc-cOX40L that utilizes the human adiponectin trimer sequence that facilitates the generation of an active trimer and hexamer of canine OX40L required for full biologic activity and binding to the OX40 receptor in the dog. It should be noted that prior to selecting OX40L for dog immunotherapy clinical trials, multiple T cell activating reagents including OX40L, CD137L, GITRL, CCL16, and CD80 were screened in a murine glioblastoma tumor model. From these studies, only OX40L significantly synergized with vaccination to rescue over 70% of mice bearing well-established gliomas. This is the most potent combination immunotherapy Applicants have observed in the GL261 mouse model. Based upon these results, the combination of OX40L and tumor cell vaccines in dogs was planned once the ADP-Fc-cOX40L fusion protein construction and testing was completed as described below.

Construction of pN24/ADP-Fc-cOX40L

A fusion gene, that contains restriction site, Kozak sequence, human adiponectin signal peptide with its collagen like domain, canis IgG A Fc region, and canis OX40L, was designed as shown in FIG. 2. This fusion gene was synthesized by Genewiz Inc. The synthetic fusion gene was digested with restriction endonucleases Hind3 and EcoR1. The 1400 kb fusion gene fragment was isolated by gel electrophoresis and purified using QIAquick gel extraction kit (Qiagen Sciences, Maryland). The purified fusion gene was then ligated into expression vector PN24 that was digested with same restriction enzymes Hind3 and EcoR1. After the reaction was complete, the enzymes were inactivated by heating for 15 min to 75° C. Ligated DNA was transformed into *E. coli* strain XL-1 and ampicillin-resistant colonies were screened by PCR and confirmed by DNA sequencing. A plasmid with the correct DNA sequence was selected for further studies.

Transfection of ADP-Fc-cOX40L in NS0 Cells

The ADP-Fc-cOX40L fusion protein was expressed in NS0 murine myeloma cells. NS0 cells were grown in non-selective medium consisting of SFM medium, 10% Fetal Bovine Serum, and 1% Glutamine/Pen/Strep. NS0 cells were maintained at an exponential growth rate with a viability of >90% prior to electroporation. The cells were cultured in a humidified 5% $CO_2$ incubator at 37° C.

The plasmid for transfection was linearized by digestion with the restriction endonuclease SalI. Forty micrograms of DNA were used per electroporation. The DNA was placed in a sterile electroporation cuvette (BioRad, Richmond, Calif.) and placed on ice for 5 minutes prior to electroporation.

On the day of electroporation, $1 \times 10^7$ NS0 cells were washed in cold PBS, resuspended at $10^7$/ml and maintained on ice. The cells were distributed to the electroporation cuvette containing the DNA preparation. The cell-DNA mixture was placed on ice for 5 min prior to electroporation. Using a Gene Pulser electroporation apparatus (BioRad), two consecutive pulses were delivered at 1,500 volts, 3 µFd, according to the manufacturer's instructions. After electroporation, the cuvette was incubated on ice for 5 min and then the cells were diluted to 30 ml in non-selective culture medium pre-warmed to 37° C.

The transfected cells were distributed to twelve 96-well plates (Costar) in non-selective medium. The plates were placed in an incubator at 37° C. with 5% $CO_2$ and 24 hr later, 150 µl of selective medium consisting of SFM medium, 10% dialyzed Fetal Bovine Serum, nucleotides, G+A solution, and 1% Pen/Strep were added to each well. The plates were returned to the incubator and left until substantial cell death had occurred and discrete surviving colonies appeared in approximately 4 weeks.

Screening for ADP-Fc-cOX40L Fusion Protein

Supernatants were removed from wells containing viable clones and tested for the production of fusion protein by ELISA. ELISA plates (Falcon) were first coated overnight at 4° C. with a 100 µl of a solution of goat anti-human Fc, diluted in carbonate buffer pH9.6. The plates were washed three times with PBS containing 0.1% Tween-20 (Sigma). Supernatants were then added to plates at 50 µl per well with 2-fold serial dilutions. Purified human IgG was used as a positive control. The supernatants were incubated in the plates for 60 minutes at room temperature at which time the plates were again washed three times and secondary antibody added. For initial screening assays, 50 µl of a solution of 1:1000 dilution of goat anti-human IgG (Fc-specific) conjugated to horseradish peroxidase PBS-Tween was used. The plates were washed again as above and the substrate reagent was added. The substrate reagent consisted of 1 mg/ml of 2,2'-azino-bis(3-ethylbenz-thiazoline-6-sulfonic acid) diammonium salt (ABTS) in citrate buffer (0.1 M citric acid monohydrate, 0.1 M $Na_2HPO_4$, the add citric acid solution to $Na_2HPO_4$ solution to pH 4.0) with 0.03% hydrogen peroxide. After 15 min the $OD^{405}$ was determined in a microplate reader (Bio-Tek).

Cell lines that secrete fusion protein were also assayed to determine the rate of production of the ADP-Fc-cOX40L fusion protein. After expansion to 10 ml, the cells were counted and $1 \times 10^6$ cells were placed in a 24-well cell culture plate in fresh selective medium for 24 hours. After incubation, the cells were again counted and supernatant removed for ELISA as above. The results of this assay are expressed as µg/ml/$10^6$ cells/24 hr. Clones that produced the highest concentrations of fusion protein in the above assay were chosen for subcloning to identify stable clones for further studies.

Purification of Fusion Protein

Figure 5:
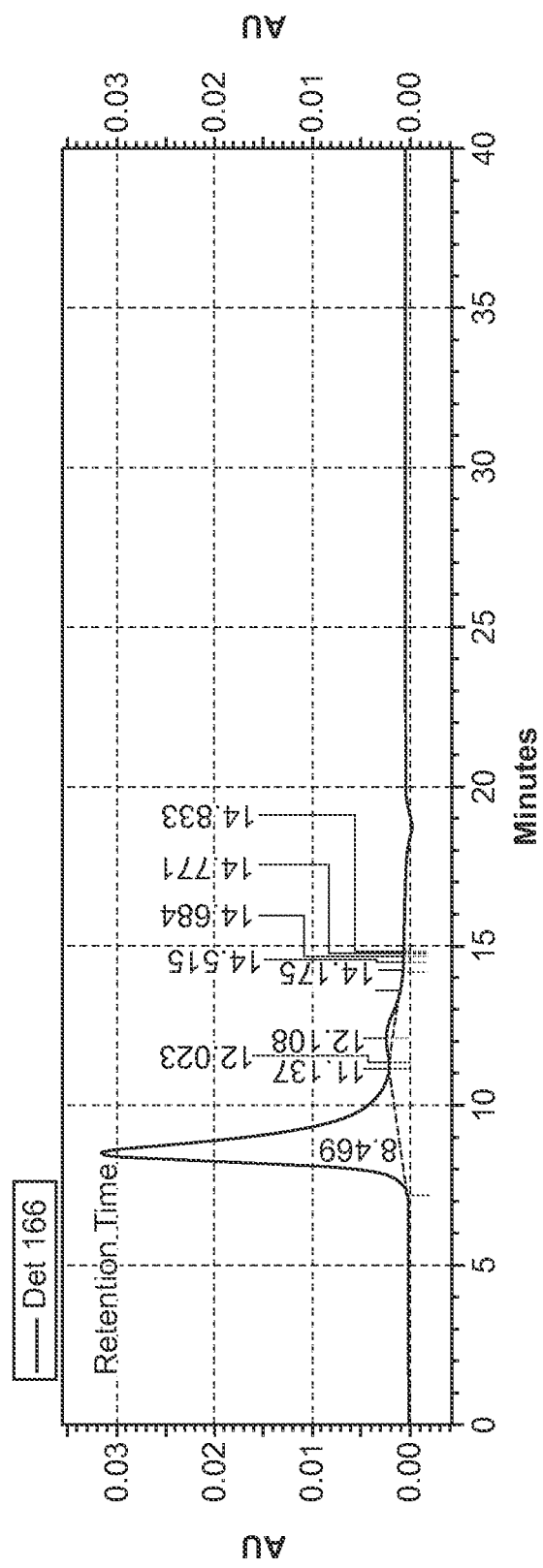
FIG. 5 depicts HPLC analysis of purified ADP-Fc-cOX40L fusion protein. HPLC analysis showed a single peak at an elution time of 8.469 seconds consistent with a large, complex molecule.

ADP-Fc-cOX40L was purified by Protein A affinity chromatography and eluted under non-denaturing conditions. Three liters of cells from stable high-secreting subclones were grown in aerated stir-flask cultures. When the viability of the flasks dropped to 50-75%, the cultures were harvested and clarified by tandom 5 micron and 0.2 micron filter units (Sartorius, Inc.). The supernatant was then applied to a Protein A Sepharose column pre-equilibrated with PBS. The column was then washed with 10 column volumes of PBS and 5 column volumes of 0.1M NaCl. The ADP-Fc-cOX40L fusion protein was then eluted with Gentle Elution Buffer (Pierce) at pH6.0. Eluted fractions were identified by measuring the absorbance at 280 nm. Protein containing fractions were pooled and exchanged into PBS using a desalting column. The amino acid sequence of the 464 amino acid fusion protein is shown below in FIG. 4. HPLC analysis of the purified ADP-Fc-cOX40L fusion protein showed a predominant peak with an elution time of 8.469 seconds consistent with a complex large molecule (FIG. 5) (Morris, N. P. et al. (2007) Mol. Immunol. 44:3112-3321).

Therapeutic Studies with Canine Fusion Protein

Thirty-two dogs diagnosed with spontaneous high-grade glioma by histologic examination of biopsy specimens are to be studied in 5 treatment cohorts as follows:
1) Vaccine+OX40L (n=8)
2) Vaccine+OX40L+TMZ (n=8)
3) Vaccine+TMZ (n=8)
4) Ox40L+TMZ (n=4)
5) TMZ (n=4)

The clinical protocol for vaccination consists of 6 µlioma lysate/CpG ODN vaccinations. The vaccinations will be administered subcutaneously on days 11, 18, 25, 45 73 and 101 days after surgery.

The clinical protocol for OX40L administration consists of administering the ADP-Fc-cOX40L fusion protein for 5 consecutive days starting concurrently with the first vaccination and repeated as a single dose at the same days of the following vaccinations: days 11 through 16, 18, 25, 45, 73 and 101. Vaccines and ADP-Fc-cOX40L will be mixed together and half of the glioma lysate/CpG/Ox40L mixture will be delivered subcutaneously on each inner thigh leg. The ADP-Fc-cOX40L dose will be calculated according with dog weight as follows:

1-20 lbs=0.2 mg/injection
21-40 lbs=0.5 mg/injection
41-80 lbs=1 mg/injection
81 lbs and above=1.5 mg/injection.

The clinical protocol for TMZ administration consists of the administration of TMZ given once a day/orally for 5 consecutive days in each cycle. The cycles start on day 33 after surgery and will be administered on a 23-day schedule.

The canine dose will be calculated based on canine body surface area (BSA) and human equivalent dosing calculations. The equivalent human dose of TMZ that will be used is 150 mg/m$^2$.

Blood samples and serum are collected for immune monitoring on days 0, 25, 45, 72, 101, 180 and 360 and resonance magnetic imaging (MRI) will be performed to evaluate tumor volume on days 1, 60, 180, and 360.

Figure 6:
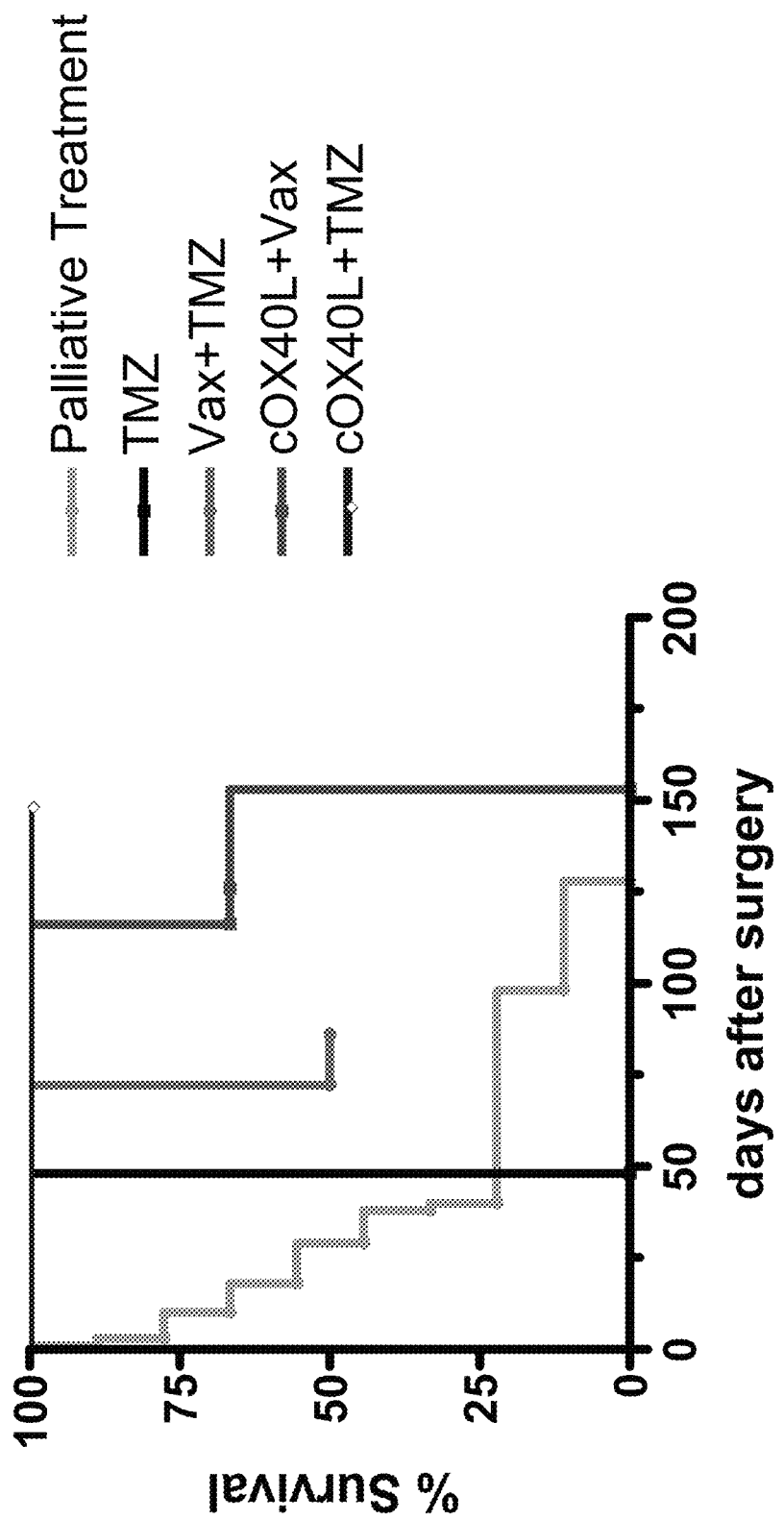
FIG. 6 shows survival data of initial dog clinical trials. Depicted is a Kaplan Meier Plot showing survival data for dogs treated with vaccination, TMZ, and/or ADP-Fc-cOX40L fusion protein. The data reveal that ADP-Fc-cOX40L plus vaccine is showing the best results to date for survival in dogs treated for spontaneous glioblastoma.

The clinical dog data are shown in FIG. 6, which shows a Kaplan Meier Plot showing survival data for dogs treated with vaccination, TMZ, and/or ADP-Fc-cOX40L fusion protein. The data reveal that ADP-Fc-cOX40L plus vaccine is showing the best results to date for survival in dogs treated for spontaneous glioblastoma.

Figure 7:
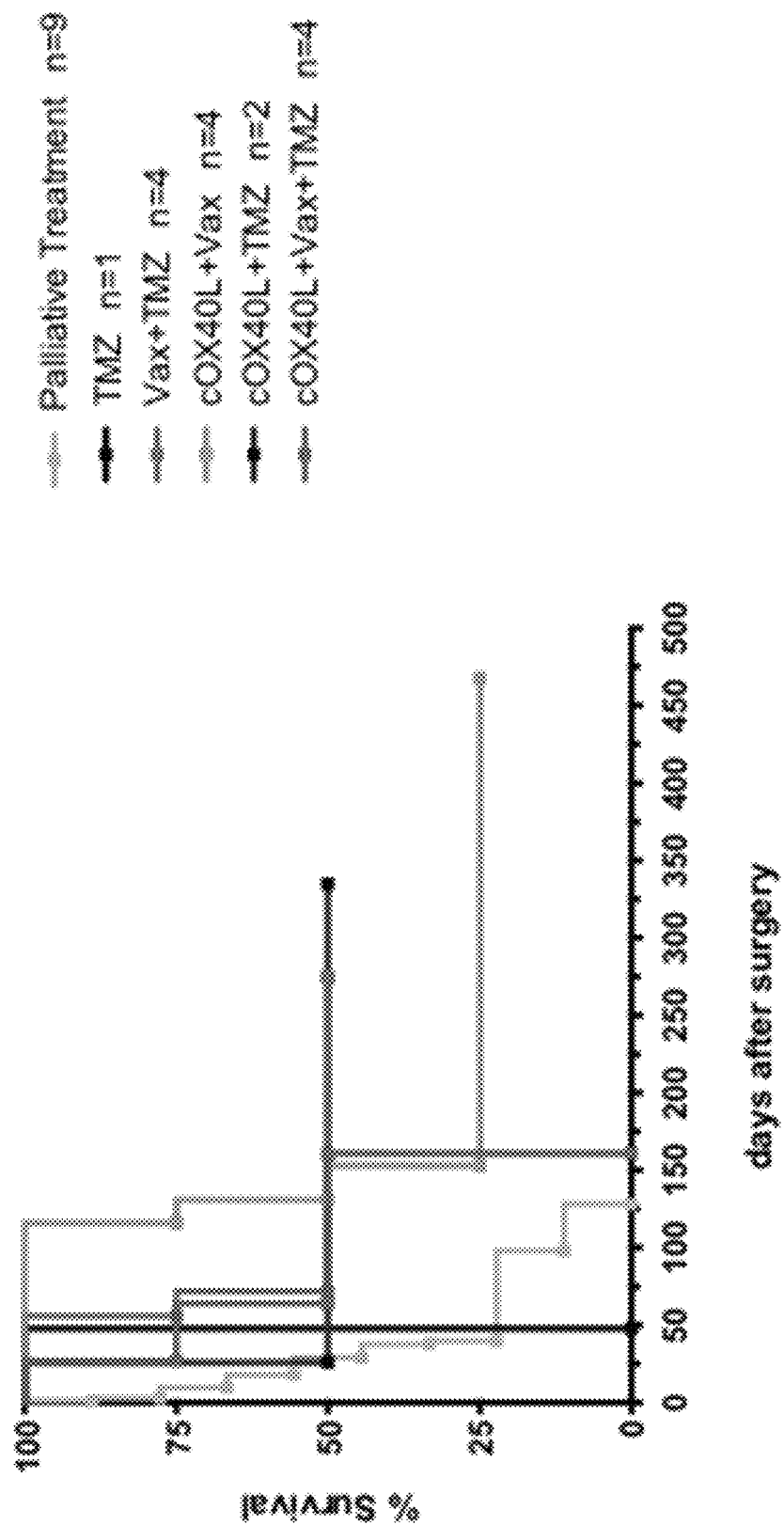
FIG. 7 shows an extension of the study in FIG. 6. Depicted is a Kaplan Meier Plot showing survival data for dogs with spontaneous glioblastoma treated with vaccination, TMZ and/or ADP-Fc-cOX40L. The data reveal that ADP-Fc-cOX40L plus vaccine is showing the best results to date for survival in dogs treated for spontaneous glioblastoma.

Further clinical dog data are shown in FIG. 7, which shows a Kaplan Meier Plot showing survival data for dogs treated with vaccination, TMZ, and/or ADP-Fc-cOX40L fusion protein. The data reveal that ADP-Fc-cOX40L plus vaccine is showing the best results to date for survival in dogs treated for spontaneous glioblastoma.

Example 2. CD8$^+$ T Cell-Independent Tumor Regression Induced by Fc-OX40L and Therapeutic Vaccination in a Mouse Model of Glioma Despite the growing number of preclinical and clinical trials focused on immunotherapy for the treatment of malignant gliomas, the prognosis for this disease remains grim. Although some promising advances have been made, the immune response stimulated as a result of immunotherapeutic protocols has been inefficient at complete tumor elimination, primarily due to Applicants' lack of understanding of the necessary effector functions of the immune system. Applicants previously demonstrated that a tumor lysate vaccine/Fc-OX40L therapy is capable of inducing enhanced survival and tumor elimination in the GL261 mouse glioma model. The following experiments were performed to determine the mechanism(s) of action of this therapy that elicits a potent antitumor immune response. The evidence subsequently outlined indicates a CD8$^+$ T cell-independent and CD4$^+$ T cell-, NK cell-, and B cell-dependent means of prolonged survival. CD8$^+$ T cell-independent tumor clearance is surprising considering the current focus of many cancer immunotherapy protocols. These results provide evidence for CD8$^+$ T cell-independent means of antitumor response and should lead to additional examination of the potential manipulation of this mechanism for future treatment strategies.

Cancer immunotherapy seeks to recruit an effective immune response to eliminate tumor cells. Unlike direct Ab therapies currently approved for clinical use, cancer vaccines have only shown limited effectiveness due to Applicants' incomplete understanding of the necessary effector cells and mechanisms that yield efficient tumor clearance. Despite these setbacks, cancer vaccines remain an enticing approach for the treatment of brain tumors, such as glioblastoma multiforme (GBM). Cytotoxic activity of CD8$^+$ T cells has long been presumed to be the effector function necessary for tumor regression, and many studies have shown that CD8$^+$ T cell responses can be elicited by a variety of immunotherapy approaches (Nelson, D. J. et al. (2001) J. Immunol. 166:5557-5566; Wang, R. F. (2001) Trends Immunol. 22:269-276; Heimberger, A. B. et al. (2011) Neuro-oncol. 13:3-13; Lee, K. H. et al. (1999) J. Immunol. 163:6292-6300).

CD4$^+$ T cells are more often regarded as helper cells to generate cytotoxic CD8$^+$ T cells and as the source of regulatory T cells (Tregs) induced by the tumor. CD4$^+$ T cells are necessary to prime and maintain a CD8$^+$ T cell response and can alter the tumor microenvironment through secretion of cytokines and the recruitment of additional immune cells, such as eosinophils and macrophages (Hung, K. et al. (1998) J. Exp. Med. 188:2357-2368). Emerging data suggest that CD4$^+$ T cells may be more important for tumor clearance than previously assumed, and in some cases more efficient than CD8$^+$ T cells (Perez-Diez, A. et al. (2007) Blood 109:5346-5354; Hirschhorn-Cymerman, D. et al. (2012) J. Exp. Med. 209:2113-2126; Muranski, P. et al. (2011) Immunity 35:972-985; Braumüller, H. et al. (2013) Nature 494:361-365). Although indirect means of tumor elimination have been more extensively studied, CD4$^+$ T cells have been shown to act as efficient cytolytic cells in both tumor and viral infection models (Mucida, D. et al. (2013) Nat. Immunol. 14: 281-289; Curran, M. A. et al. (2013) J. Exp. Med. 210:743-755; Soghoian, D. Z. et al. (2010) Expert Rev. Vaccines 9:1453-1463). Despite the growing evidence for CD4$^+$ T cell-based mechanisms of cell killing that are independent of CD8$^+$ T cells, the field of tumor immunotherapy has not fully embraced these important findings.

Many components of the immune system can contribute to effective immunotherapy. In addition to T cells, B cells can also induce antitumor responses. B cells can differentiate into Absecreting plasma cells or present Ags to T cells, contributing to T cell activation and memory (Crawford, A. et al. (2006) J. Immunol. 176:3498-3506). An intact blood brain barrier restricts the passive diffusion of large proteins, including Igs, into the brain, and thus the role of an Ab response in the efficacy of brain tumor immunotherapy has largely been ignored (Deeken, J. F. et al. (2007) Clin. Cancer Res. 13:1663-1674). Paradoxically, one study has shown a correlation between the presence of tumor-reactive Abs in GBM patients and survival (Pallasch, C. P. et al. (2005) Int. J. Cancer 117:456-459).

Some important components of the innate immune system are often overlooked in tumor clearance. Characterization of an antitumor response induced by CD40 ligation through administration of an agonist CD40 Ab showed that tumor regression was dependent on macrophages and independent of CD4$^+$ or CD8$^+$ T cells (Beatty, G. L. et al. (2011) Science 331:1612-1616). Additionally, eosinophils, mast cells, and NK cells have been shown to have antitumor capabilities (Tepper, R. I. et al. (1992) Science 257:548-551; Purwar, R. et al. (2012) Nat. Med. 18:1248-1253; Liu, R. B. et al. (2012) Cancer Res. 72:1964-1974).

The immune-specialized nature of the brain presents unique challenges in developing effective immunotherapies for brain tumors. The brain, even in the absence of tumor, has an immunological preference displayed by the secretion of immunosuppressive molecules, such as TGF-β. This biases the brain and the draining lymph nodes for induction of a Th2 response (Harling-Berg, C. J. et al. (1999) J. Neuroimmunol. 101:111-127). In addition, even when a CD8$^+$ T cell response is generated, the immunosuppressive nature of the brain can prevent effector function and limit tumor elimination (Gordon, L. B. et al. (1997) J. Immunol. 159:2399-2408).

The clinical success of cancer treatments such as CTLA-4 and PD-1 blockade has led to an increased interest in immunemodulatory agents (Hodi, F. S. et al. (2010) N. Engl. J. Med. 363:711-723; Topalian, S. L. et al. (2012) N. Engl. J. Med. 366:2443-2454). Signaling through costimulatory molecules, including members of the TNFR superfamily, such as 41BB, OX40, and glucocorticoid-induced TNFR, can lead to T cell expansion and upregulation of effector cytokine production, and can break tolerance (Pardee, A. D. et al. (2009) Immunotherapy 1:249-264). These receptors can be targeted by agonist Abs or ligand fusion proteins, in which the corresponding ligands are fused to Ig proteins for systemic delivery in vivo (Pardee, A. D. et al. (2009) Immunotherapy 1:249-264).

Recently, Applicants described an efficacious combination therapy involving tumor lysate and adjuvant vaccines with Fc-OX40L costimulation in a murine brain tumor model (Murphy, K. A. et al. (2012) Clin. Cancer Res. 18:4657-4668). The work described in this study aims to dissect the mechanisms at work in this potent antitumor therapy in a mouse GBM model. Applicants' results indicate a $CD4^+$ T cell-, B cell-, and NK cell-dependent means of tumor eradication, whereas $CD8^+$ T cells appear to be unnecessary for enhanced tumor-free survival. The following work should aid in the understanding of mechanisms at play in an effective antitumor response and guide future therapeutic designs. Applicants' previous research and current work suggest an alternative means of tumor eradication to the canonical CD8+ cytotoxic T cell mechanism, and may shed light on routes of immune modulation that result in effective tumor clearance in GBM.

Materials and Methods

Animal Models and Cell Lines

GL261-Luc culture conditions have been described previously (Wu, A. et al. (2007) J. Immunother. 30:789-797). Animals were maintained in a specific pathogen-free facility, according to the University of Minnesota Institutional Animal Care and Use Committee guidelines. Seven-week-old wild-type (WT) C57BL/6J, B6.129S2-Cd8a$^{tm1Mak}$/J (CD8a knockout [KO]), C57L/6-Prf$^{tmSz}$/J (perforin KO), and B6.129S2-Igh$^{tmICgn}$/J (µMT) mice were purchased from The Jackson Laboratory (Bar Harbor, Me.). Five- to 7-wk-old B6.129P2-Fcer1g$^{tm1Rav}$N12 (FcRγ KO) mice were purchased from Taconic. IgMi mice were previously developed by A. Waisman (University of Mainz, Mainz, Germany) and K. Rajewsky (Harvard Medical School, Boston, Mass.) (Waisman, A. et al. (2007) J. Exp. Med. 204:747-758; Waisman, A. et al. (2008) Med. Microbiol. Immunol. 197: 145-149). Tumors were established by intracranial inoculation of 15,000 GL261-Luc glioma cells in 1 µl HBSS (Life Technologies) into animals anesthetized with a ketamine/xylazine mixture (54.7 mg/ml ketamine and 9.26 mg/ml xylazine). Cells were implanted into the right hemisphere at coordinates 2.5 mm lateral, 0.5 mm anterior from bregma, and 3 mm ventral to the surface of the brain and delivered at a rate of 0.2 µl/min over 5 min (Wu, A. et al. (2007) J. Immunother. 30:789-797). Bioluminescence imaging 3 d following inoculation confirmed tumor implantation. Animals received 100 µl luciferin (Gold Biotechnology) by i.p. injection and were imaged with an IVIS50 system (Caliper Life Sciences). Living Image software (Caliper Life Sciences) was used to determine tumor burden in animals as a measure of photons/s (p/s); periodic bioluminescence imaging tracked tumor progression.

Vaccine Production and Delivery

Vaccines were generated, as previously described (Murphy, K. A. et al. (2012) Clin. Cancer Res. 18:4657-4668). Tumor cells were washed three times with PBS, resuspended in PBS, and flash frozen with liquid nitrogen. Cells were subjected to five cycles of freezing in liquid nitrogen and thawing in a 37° C. water bath, vortexing after each round, to induce cell lysis. Trypan blue dye exclusion was used to verify complete cell death. A Pierce bicinchoninic acid assay kit (Thermo Scientific) was used to determine protein concentration of the lysates. Purified, endotoxinfree CpG 1826, an unmethylated oligodeoxynucleotide sequence (59-tccatgacgttectgacgtt-3') with a full phosphorothioate backbone (Integrated DNA Technologies, Coralville, Iowa), was resuspended in 1×Tris-EDTA buffer. Vaccines, consisting of 65 µg tumor lysate and 50 µg CpG 1826 brought to a final volume of 100 µl with saline, were delivered by intradermal injection above the shoulders.

Costimulatory Fusion Protein Production and Delivery

Fc-OX40L was developed and verified previously (Sadun, R. E. et al. (2008) J. Immunother. 31:235-245). Fc-OX40L was given at 50 mg/dose, brought to a final volume of 100 µl/dose with PBS, and delivered by i.p. injection. Animals received vaccine (intradermal) and Fc-OX40L (i.p.) on days 7, 10, and 13 postinoculation and Fc-OX40L (i.p.) days 15-19, unless otherwise stated.

Lymphocyte Depletion

Specific lymphocyte populations were depleted by i.p. injection of depleting Abs. A total of 100 mg anti-NK1.1 (clone PK136; eBioscience) or anti-CD4 (clone GK1.5; eBioscience) or 200 mg anti-CD8 (clone 53-6.7; eBioscience) was delivered for 2 d before the first immunization, then 1 d before each additional vaccine, and 1 d prior to beginning Fc-OX40L treatment. Depletion was verified by euthanizing one animal from each group on day 3 before the first vaccination and analyzing splenocytes by flow cytometry.

Flow Cytometry

Brain-infiltrating lymphocytes were harvested from animals on day 25 postinoculation. Mice were euthanized with a ketamine/xylazine mixture and perfused with PBS to flush the capillaries. The brains were removed, minced with a razor, dissociated with TrypLE (Invitrogen), and passed over a 70-µm filter. Leukocytes were collected from a two-layer Percoll gradient (70 and 30%). Cell counts were obtained using trypan blue dye exclusion and a hemocytometer. Cells were stained with the following Abs for phenotypic analysis: CD3 (clone 17A2; eBioscience), CD4 (clone GK1.5; eBioscience), CD8 (clone 5H10; Invitrogen), NK1.1 (clone PK136; eBioscience), MHC II (clone M5.114.15.2; eBioscience), CD11b (clone M1/70; eBioscience), CD11c (clone N418; eBioscience), Foxp3 (clone FJK-16s; eBioscience), and perforin (clone eBioOMAK-D; eBioscience). Intracellular staining of Foxp3 was achieved by utilizing the Foxp3/transcription factor intracellular staining kit, according to the manufacturer's instructions (eBioscience). The BD Cytofix/Cytoperm plus kit (BD Biosciences) was used to gain intracellular staining of perforin. Flow cytometric analyses were performed on a BD Biosciences FACSCanto, and data were analyzed using Flowjo software (Tree Star). The percentage of stained cells was multiplied by the total number of viable cells, determined previously by trypan blue dye exclusion, to obtain the total number of stained cells, then divided by tumor burden (p/s) to obtain the number of cells relative to tumor size.

To detect tumor-reactive serum Abs, cultured GL261 cells were harvested and incubated with serum (1:100, by volume), washed thoroughly, and stained with a fluorescently labeled rat anti-mouse IgG (Jackson ImmunoResearch Laboratories) or IgM (clone II/41; eBioscience) Ab. Samples were analyzed on a BD Biosciences FACSCanto, and mean fluorescence intensities were determined using Flowjo software (Tree Star).

Histopathology

Tumor-bearing animals were euthanized and perfused with phosphate-buffered water and 4% paraformaldehyde. Formalin-fixed tumor-bearing brains were serially sectioned and processed into paraffin blocks using standard histology techniques, sectioned to 4-mm thickness, and stained with H&E. Slides were evaluated by a board-certified anatomic pathologist by light microscopy.

Suppression Assay

T cells were isolated from a naive WT spleen using the mouse CD8a T cell isolation kit from Miltenyi Biotec and stimulated in vitro with plate-bound CD3 (1 μg/ml) (eBioscience; 2C11) in a round-bottom plate. CD11b$^+$ cells isolated from spleen and brains of tumor-bearing animals with the CD11b isolation kit from Miltenyi Biotec were plated with $5 \times 10^4$ CD8$^+$ T cells. Tritiated thymidine was added to cells after 48 h and allowed to incubate for an additional 24 h. Proliferation was determined by thymidine incorporation. Suppression was calculated by normalizing to CD3-stimulated T cells in the presence of CD11b$^+$ cells isolated from naive animals, percent suppression=([(T cells+CD3+naive CD11b$^+$) 2-(T cells+CD3+tumor CD11b$^+$)]/[T cells+CD3+ naive CD11b$^+$]) 3×100.

Western Blots

Tumor Tissue was Sonicated in Radioimmunoprecipitation Assay Buffer (25 mM Tris-HCl, 0.1% SDS, 1% Triton X-100, 1% sodium deoxycholate, 0.15 M NaCl, 1 mM EDTA) with protease and phosphatase inhibitors (1:100; Calbiochem). Protein concentrations were determined using the Pierce bicinchoninic acid assay kit (Thermo Scientific). For SDS-PAGE, lysates were made 2 mg/ml with Laemmli reducing sample buffer. Protein standards (Bio-Rad) were loaded next to each 40 μg lysate and resolved on NuPAGE 4-12% Bis/Tris gels (Invitrogen). Gels were equilibrated for 30 min in Towbin's transfer buffer, and proteins were then transferred to nitrocellulose membranes (Amersham) at 5 V constant voltage overnight using semidry transfer (Bio-Rad). The membranes were blocked in 5% nonfat dry milk/Tris-Tween 20-buffered saline (TTBS) at room temperature for 1 h. Membranes were then incubated at room temperature for 1 h in HRP-conjugated secondary Ab (Jackson ImmunoResearch) at 1:50,000 in 5% nonfat dry milk/ TTBS and washed six times for 10 min each in TTBS. Immunoreactive bands were detected using ECL Plus Western blotting Detection System (Amersham) exposing membranes to HyBlot CL autoradiography film (Denville).

Statistical Analyses

A Mann-Whitney U test was used for the statistical comparison of lymphocyte counts and mean fluorescence intensities. Tumor burden between groups was compared using an unpaired Student t test. Animal survival was evaluated by log-rank test. All tests were performed with Prism 4 software (GraphPad Software). The p values, 0.05 were considered statistically significant.

Results

Lymphocyte Depletion Reveals the Importance of CD4+ T Cells and NK Cells in Vaccine/Fc-OX40L Treatment of GBM The role of specific lymphocyte subsets contributing to tumor eradication by vaccine/Fc-OX40L treatment was assessed by depleting CD8$^+$, CD4$^+$, and NK cells. Depletion was verified by flow analysis of isolated splenocytes from one animal in each depletion group. Survival of the tumor-bearing depleted animals was compared with replete tumor-bearing animals. Interestingly, CD4 depletion completely abrogated the survival benefit conferred from treatment. Specifically, treated mice with CD4 depletion survived an average of 32 days post-inoculation while treated mice with no depletion survived an average of 58 days post-inoculation. NK depletion also had an effect on survival, albeit to a lesser magnitude than CD4 depletion. NK-depleted animals survived significantly longer than nondepleted untreated animals, but never as long as nondepleted animals that were treated with vaccine/Fc-OX40L. Surprisingly, CD8 depletion did not negatively affect overall survival. Specifically, treated mice with CD8 depletion survived an average of 90 days post-inoculation while treated mice with no depletion survived an average of 58 days post-inoculation. To confirm these unexpected findings suggesting the limited role of CD8$^+$ T cells, CD8 KO mice were challenged with GL261 and treated with vaccine/Fc-OX40L. The CD8 KO mice had prolonged survival, confirming the previous results using CD8-depleted mice. Specifically, about 62% of treated CD8KO mice survived by day 125 post-inoculation. These data suggest that the immune response responsible for increased survival and tumor clearance is CD8$^+$ T cell independent or that CD8$^+$ T cells somehow block the response to immunotherapy. Thus, contrary to many tumor models in which immunotherapy is employed, these data suggest Applicants' vaccine therapy elicits an immune response dominated by CD4$^+$ T cells and NK cells and not CD8$^+$ T cells.

B Cell-Dependent Mechanism of Vaccine/Fc-OX40L Treatment

To determine the extent to which B cells were necessary for the Fc-OX40L treatment, WT and μMT (B cell-deficient) animals were inoculated with GL261 tumor cells and treated with vaccine and Fc-OX40L. Treatment benefit was lost in the μMT animals, suggesting that B cells are necessary for proper immune response and eradication of tumor. Specifically, treated μMT mice survived an average of 38 days post-inoculation while WT mice survived an average of 61 days post-inoculation.

Ab Response to Vaccine/Fc-OX40L Treatment

The B cell dependency noted for treatment efficacy may be mediated through different mechanisms of B cell action. B cells can act as APCs, although this role is less well described for B cells than for dendritic cells. B cells also differentiate into Ab-secreting cells (plasma cells) and exert effector function through Ab-mediated mechanisms. To test the extent to which Abs were playing a role in Applicants' tumor model, serum was collected from saline-, vaccine-, Fc-OX40L-, and vaccine/Fc-OX40L-treated animals at day 25 postinoculation. This time point was chosen because the treatment regimen had been completed, but the untreated animals were not yet moribund. Serum was also collected at days 35 and 45 for vaccine/Fc-OX40L-treated animals to assess the later time points when the tumors began to regress. There were no significant differences in the presence of IgM Ab binding to tumor cells among treatment groups as measured through flow cytometry (data not shown). All groups had elevated levels of tumor-reactive IgG Abs relative to serum from a normal (nontumor-bearing) animal. Tumor-reactive IgG levels at day 25 were similar among groups, but there was a trend to increasing IgG levels at days 35 and 45 in vaccine/Fc-OX40L-treated animals. The similarity in IgG levels at day 25 suggests an endogenous Ab response in tumor-bearing animals, which may indicate that Fc-OX40L is not involved in inducing Ab secretion. The trend toward increasing levels of IgG over time in the vaccine/Fc-OX40L-treated animals indicates that Fc-OX40L may aid in the maintenance of, or help promote, the Ab response over time.

Ab Deposition in Tumor

To determine whether Ab was being deposited in the tumors of the vaccine/Fc-OX40L-treated animals and to gain insight into the kinetics of this event, animals were inoculated with GL261 tumor, treated with vaccine/Fc- OX40L, and euthanized on days 25, 35, and 45. Saline- and vaccine-only controls were also collected on day 25. Western blot analysis revealed the presence of IgG in the tumors of animals treated with vaccine/Fc-OX40L. Bands consistent with IgG H and L chain (50 and 25 kDa, respectively) were detected in the tumors of animals treated with vaccine/Fc-OX40L. The 50-kDa band consistent with the H chain of IgG was not detected in the tumors of saline-treated animals. The presence of a 25-kDa band in these tumors is most likely due to the cross-reactivity of the Ab with the L chain of the other Igs. IgG was detected in the majority of the vaccine-only-treated tumors as well. Interestingly, whereas all of the tumors analyzed from vaccine/Fc-OX40L-treated mice at day 25 contain IgG, the number of animals with detectable IgG at the later time points decreases at day 35 (4 of 5) and day 45 (3 of 5). This may be due in part to the decreasing tumor burden at these later time points.

IgM was detected in the tumors of animals of all treatment groups, although with varying penetrance. The H chain of IgM was detectable and appears to be most penetrant at day 35 in vaccine/Fc-OX40L-treated animals. It is important to note that several gels were run to analyze these samples, so whereas the presence or absence of Ig can be noted, the relative amounts cannot be accurately compared. The presence of IgM and absence of IgG in the tumors of saline-treated mice suggest that infiltration of class-switched Ig may be impaired.

Analysis of Brain-Infiltrating Cells

Flow cytometry analysis was performed on lymphocytes isolated from the brains of tumor-bearing animals. Glioma-bearing WT animals treated with saline, vaccine only, Fc-OX40L only, and vaccine/Fc-OX40L were euthanized on day 25. One day prior to euthanasia, tumor burden was assessed by bioluminescence imaging and revealed a significant difference in the tumor size among the groups. Animals receiving Fc-OX40L as part of the treatment showed significantly less tumor burden. Lymphocytes harvested from the brains were counted and plotted as absolute numbers. The number of brain-infiltrating cells observed in the WT animals receiving vaccine/Fc-OX40L treatment was not significantly greater than saline-treated animals. The large variation in tumor size may distort the true value of infiltrating cells present in the brain, as larger tumors may contain more infiltrating cells simply due to volume. To compensate for this difference, the number of brain-infiltrating cells was normalized to the tumor burden determined by bioluminescence imaging (p/s). This analysis revealed that, based on tumor burden, there were more lymphocytes infiltrating the tumors of Fc-OX40L-treated WT animal.

Phenotypic staining assessed the composition of the lymphocyte population harvested from the brains of glioma-bearing animals. The T cell population was determined by analyzing the $CD3^+CD4^+Foxp3^{neg}$ and $CD3^+CD8^+$ populations. An increase in the infiltration of $CD4^+$ T cells was observed for the WT animals treated with Fc-OX40L, consistent with the earlier finding that $CD4^+$ T cells are necessary for efficacy of treatment. Interestingly, an increase in infiltration of $CD8^+$ T cells was observed in the vaccine/Fc-OX40L-treated animals, despite the fact that these cells are not necessary for tumor clearance. Although these cells are present, this analysis does not indicate whether this population is active. Analysis for the presence of perforin, used in the cytolytic function of $CD8^+$ cells, revealed that this population does not express perforin, which may suggest that they are not actively functioning as killer cells. Importantly, $CD4^+$ T cells also did not demonstrate expression of perforin.

Ligation of OX40 on the surface of Tregs can decrease the suppressive function of this population (Ruby, C. E. et al. (2009) J. Immunol. 183:4853-4857; Burocchi, A. et al. (2011) Eur. J. Immunol. 41:3615-3626). It is reasonable to assume that one mechanism of Fc-OX40L in tumor eradication is to suppress the regulatory function of these cells, thus allowing the effector cells to kill. Analysis of the $CD3^+ CD4^+ Foxp3^+$ Treg population in the brains demonstrates an increase in the presence of Tregs in the tumors of animals treated with Fc-OX40L. This is contrary to what was expected; however, it is possible that the increased immune infiltration observed triggers an influx of Tregs to balance the inflammatory response. This analysis also does not indicate whether this population is actively suppressing effector cells; functional analysis of isolated cells would be required to fully understand the effect on Tregs.

The NK cell population was of particular interest as its depletion resulted in loss of treatment efficacy. Specifically, treated mice with NK depletion survived an average of 44 days post-inoculation while treated mice with no depletion survived an average of 58 days post-inoculation. The total $CD3^{neg}NK1.1^+$ population, which excludes NKT cells, was assessed and observed to be increased in Fc-OX40L-treated animals only when normalized to tumor burden. Impressively, the $CD3^{neg}NK1.1^+$ perforin$^+$ population was increased in the Fc-OX40L-treated groups, demonstrating that NK cells are present and presumably functional. An intriguing observation was the presence of a distinct $CD3^+ NK1.1^+$ population, NKT cells, in the brains of Fc-OX40L-treated animals, and, surprisingly, a significant number of these cells expressed perforin.

The most noticeable difference among the treatment groups was a granular cell population in the vaccine/Fc-OX40L treatment groups that was absent in the saline and the vaccine treatment groups. Phenotypic analysis revealed that the majority of cells in this population are $CD11b^+$ MHC II$^{neg}$, indicative of neutrophils, which like NK cells are able to kill Ab-coated cells through Ab-dependent cell-mediated cytotoxicity (ADCC) (Challacombe, J. M. et al. (2006) J. Immunol. 177:8123-8132; Delves, P. J. et al. (2000) N. Engl. J. Med. 343:108-117).

Involvement of the FcR and Ab

The indication that Ab production may play a significant role in tumor elimination combined with the loss of treatment efficacy with NK cell depletion led to the investigation of the role that ADCC may play in treatment-induced tumor regression. ADCC requires the Fc portion of Igs bound to target Ag to bind to FcR on the surface of effector cells, most commonly NK cells. This binding induces lysis of the target cell by the effector cell, generally through the production and release of perforin and granzymes. To test whether this mechanism was the link between the NK cell and the Ab results, treatment efficacy was tested in mice deficient for the γ-chain of the FcR (FcRγ KO). These mice lack the FcRs capable of binding IgG and IgE, and therefore ADCC action mediated through these Igs would not be possible. Whereas there was a significant difference in the overall survival of saline-treated WT and FcRγ KO animals (p=0.0146), suggestive of an endogenous response involving the FcR, the overall survival of WT and FcRγ KO animals that received vaccine/Fc-OX40L treatment did not differ significantly. Specifically, treated WT mice survived an average of 71 days post-inoculation while treated FcRγ KO mice survived an average of 49.5 days post-inoculation. However, there is clearly a trend toward an intermediate phenotype that is best illustrated in the tumor burden of these animals. Biolumi-nescence imaging was performed to track changes in tumor burden. These studies showed that the rate of tumor growth was rapid in saline-treated mice, but was slowed by vaccine/Fc-OX40L treatment especially in the WT mice compared with the FcRγ KO mice.

To verify whether indeed Abs were necessary for the efficacy of Applicants' treatment, Applicants tested the therapy in an animal model deficient for plasma cells (IgMi mice) (Waisman, A. et al. (2007) J. Exp. Med. 204:747-758; Waisman, A. et al. (2008) Med. Microbiol. Immunol. 197:145-149). Applicants observed an intermediate phenotype in response to treatment in these mice. The IgMi vaccine/Fc-OX40L-treated animals survived significantly longer than the saline-treated animals, but did not reach the full survival benefit of the WT animals. Specifically, treated IgMi mice survived an average of 47 days post-inoculation while saline treated IgMi mice survived an average of 40 days post-inoculation. Meanwhile, treated WT mice survived an average 63 days post-inoculation. Once again, the intermediate phenotype in response to treatment is reflected in the tumor burden of these animals, as measured by bioluminescence imaging.

Overall, survival after vaccine/Fc-OX40L treatment of the plasma cell-deficient mice paralleled that of FcRγ KO, suggesting that the Ab dependence is likely through a FcR-based mechanism. Whereas Ab-mediated mechanisms are not required for complete tumor clearance, Ab does play a role in controlling tumor growth early in the course of treatment based on the greater tumor burden seen in the IgMi and FcRγ KO mice.

A mechanism of NK killing through ADCC is through the release of perforin and granzymes, and Applicants observed an increase in the perforin-expressing NK cells after treatment; however, when the efficacy of the vaccine/Fc-OX40L treatment was tested in perforin-deficient (perforin KO) animals, Applicants found that treatment was not perforin dependent. Specifically, treated WT mice survived an average of 83 days post-inoculation while treated perforin KO mice survived an average of 79.5 days post-inoculation.

Tumor Infiltration of Granular Population with Fc-OX40L Treatment

The granular population observed by flow cytometry was further analyzed to determine its role in the therapeutic response. Histologic analysis revealed that tumors from multiple vaccine/Fc-OX40L-treated animals were infiltrated by a moderate to large number of neutrophils, which in some areas of the tumor formed dense aggregates and replaced neoplastic cells. Neutrophils were characterized by a multilobed nucleus and a homogenous eosinophilic cytoplasm. Tumors in saline-treated mice were infiltrated by a moderate number of mononuclear cells, but neutrophils were not a prominent component of the inflammatory cell infiltrate as determined by a pathologist. It is important to note that this population is also consistent with the myeloid-derived suppressor cell population, which is often induced by the tumor itself and generally only distinguishable from neutrophils by functional assays. Thus, a suppression assay was performed, revealing that the CD11b$^+$ cells isolated from the brains of vaccine/Fc-OX40L-treated animals were not functionally suppressive. Furthermore, when nontumor-bearing animals were treated with Fc-OX40L, there was a dramatic increase in the presence of CD11b$^+$ cells in the blood, suggesting that the treatment, rather than the tumor, is responsible for neutrophil recruitment.

Discussion

Despite the increasing interest in utilizing immunotherapeutic approaches in cancer treatment, the prognosis for patients diagnosed with glioma remains poor. Advances in the field of cancer immunotherapy have been incremental, and an inherent hurdle to progress is the lack of a basic understanding of the mechanisms needed for an effective immune-based antitumor response. One route of gaining insight into these mechanisms is to examine the immune players at work during an effective antitumor response. Because prior studies by Applicants' laboratory have identified a potent antitumor treatment in a murine model of glioma (Murphy, K. A. et al. (2012) Clin. Cancer Res. 18:4657-4668), Applicants were in the position to define the mechanisms responsible for tumor clearance.

In the present report, Applicants' data demonstrate that this response is dependent on CD4+ T cell and NK cell responses, as efficacy is lost upon depletion of these cells. In contrast to many other studies, Applicants' data indicate that the CD4+ T cell response in this model was critical for tumor regression. In this immunotherapeutic model, however, further work remains to be done to identify the exact mechanism of CD4$^+$ T cell action. CD4$^+$ T cells could potentially be orchestrating the activation and infiltration of other immune cells that carry out the cytotoxic functions. In contrast, CD4$^+$ T cells are capable of cytolytic function through their direct and indirect killing in viral and tumor models (Perez-Diez, A. et al. (2007) Blood 109:5346-5354; Soghoian, D. Z. et al. (2010) Expert Rev. Vaccines 9:1453-1463; Brady, M. S. et al. (2000) Cancer Immunol. Immunother. 48:621-626). It is possible that Applicants' model may be reproducing the results observed in these previous publications. Whereas the exact mechanisms remain to be elucidated, the perforin-independent tumor regression would suggest that if CD4$^+$ T cells are mediating a cytotoxic response, pathways such as TRAIL and FasL should be examined.

Many cancer vaccines have been designed to induce a robust CD8$^+$ T cell response. Surprisingly, Applicants did not observe a dependency of CD8$^+$ T cells, as CD8 depletion did not alter survival outcome. An increase in the median survival of animals depleted of CD8$^+$ T cells was observed, initially suggesting that CD8$^+$ T cells may have a deleterious effect on survival. However, the overall survival did not achieve statistical significance and further analysis of survival in CD8 KO animals did not reveal any difference in median survival. Although tumor-infiltrating CD8$^+$ T cells were observed in vaccine/Fc-OX40L-treated animals, the results of the depletion study suggest these cells may be functionally inactive. It is also possible that, in an attempt to prevent tissue damage from an inflammatory response, the CD8$^+$ T cells may be suppressive. Previous laboratories have shown that CD8$^+$ T cells express the suppressive cytokine IL-10 in response to viral infections in the lung and brain, where prolonged activation may cause deleterious bystander effects (Trandem, K. et al. (2011) J. Immunol. 186:3642-3652; Palmer, E. M. et al. (2010) Virology 404:225-230). These remain attractive theories that need to be tested, and the optimized strategy of vaccine/Fc-OX40L in the GL261 glioma model presents as a robust model to pursue these questions in the future.

Additionally, B cells are required for the efficacy of treatment. B cells may be necessary to act as APCs for CD4$^+$ T cell activity or they may be differentiating into plasma cells and secreting tumorreactive Abs or Abs required for ADCC. The observation that tumor-bearing animals generate tumor-reactive Abs and the deposition of Ab in the tumors of vaccine/Fc-OX40L-treated animals points in this direction. The loss of control of tumor growth in FcRγ KO and IgMi mice suggests that ADCC mechanisms may be a contributing factor in the therapeutic response; however, due to the incomplete loss of efficacy, there are obviously other mechanisms contributing to tumor clearance.

The infiltration of tumor by immune cells is key in understanding the mechanism of tumor clearance. The most notable observation was the infiltration of NK cells, NKT cells, and the large granular population. Recruitment and activation of NK cells, NKT cells, and neutrophils may be mediated by cytokine secretion by CD4+ T cells activated through OX40 ligation. Another explanation could involve direct activation by OX40L. Although the majority of research conducted on OX40:0 X40L interactions has focused on activated T cells, there have been some reports indicating that NK cells (Liu, C. et al. (2008) J. Clin. Invest. 118:1165-1175), NKT cells (Zaini, J. et al. (2007) J. Clin. Invest. 117:3330-3338), and neutrophils (Baumann, R. et al. (2004) Eur. J. Immunol. 34:2268-2275) may express the OX40 receptor. It is possible that Fc-OX40L administration is acting directly on the innate immune cells to induce a productive antitumor response, although this remains controversial.

The observed infiltration of innate immune cells is particularly interesting in light of Applicants' Ab data, due to the known link between the NK cells, neutrophils, and ADCC. It is possible that these cells are actively killing Ab-coated tumor cells and inhibiting growth in a FcR-dependent mechanism. The presence of a large granulocyte population remains an interesting potential mechanism of tumor clearance. These cells were found to infiltrate into the tumors of animals treated with Fc-OX40L, and these mice also demonstrated the greatest response to treatment.

As shown by Applicants' data, multiple mechanisms of tumor clearance may be occurring in this tumor model. Too often in the design of immunotherapeutic studies, particular immune subsets are targeted while ignoring the remainder of the immune system. This is particularly noted for CD8+ T cell-biased therapies. Many vaccines have focused on CD8+ T cell-restricted Ags or adoptive transfer exclusively (Wang, R. F. (2001) Trends Immunol. 22:269-276). Even in the case of CD8+ T cell-mediated tumor clearance, recruitment of additional immune cells is necessary, particularly CD4+ Th1 cells that are needed for maintenance of the CD8+ T cell response. The observation of an increase in the influx of innate cells to the tumor site upon treatment and the presence of a tumor-reactive Ab response may be linked through a FcR-dependent mechanism. A deeper understanding of immune-mediated mechanism of tumor clearance will certainly drive the design of immunotherapy regimens in the clinic with the hope of fully harnessing the power of the immune system to mediate lasting tumor clearance with memory. Considering that the CNS may provide unique challenges for tumor immunology, it is entirely possible that different cell populations may be involved in effective tumor clearance than that found in solid tumors of peripheral tissues.

The disclosure illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. Other embodiments are set forth within the following claims.

What is claimed is:

1. An isolated recombinant polypeptide SEQ ID NO: 3.

2. A composition comprising:
   a) the isolated recombinant polypeptide of claim 1; and
   b) a pharmaceutically acceptable carrier.

3. The composition of claim 2, further comprising a vaccine comprising a cancer cell lysate or immune cells.

4. The composition of claim 2, further comprising an adjuvant.

5. The composition of claim 4, wherein the adjuvant is an oligonucleotide comprising one or more immunostimulatory sequence motifs, the motif comprising at least one unmethylated CG dinucleotide.

6. The composition of claim 5, wherein the oligonucleotide contains multiple immunostimulatory sequence motifs.

7. The composition of claim 6, wherein the immunostimulatory sequence motif comprises one or both of SEQ ID NO: 4 or SEQ ID NO: 5.

8. A kit comprising the composition of claim 2 and instructions for use.

* * * * *

SEQUENCE LISTING

```
<160> NUMBER OF SEQ ID NOS: 6

<210> SEQ ID NO 1
<211> LENGTH: 1395
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atgctgttgc tgggagctgt tctactgcta ttagctctgc ccggtcatga ccaggaaacc        60
acgactcaag ggcccggagt cctgcttccc ctgcccaagg gggcctgcac aggttggatg       120
gcgggcatcc cagggcatcc gggccataat ggggccccag gccgtgatgg cagagatggc       180 accccctggtg agaagggtga gaaaggagat ccaggtctta ttggtcctaa gggagacatc       240
ggtgaaaccg gagtacccgg ggctgaaggt ccccgaggct ttccgggaat ccaaggcagg       300
aaaggagaac ctggagatac accccatgc ccagtccctg aacctctggg agggccttcg       360
gtcctcatct tccccccgaa acccaaggac atcctcagga ttacccgaac acccgaggtc       420
acctgtgtgg tgttagatct gggccgtgag gaccctgagg tgcagatcag ctggttcgtg       480
gatggtaagg aggtgcacac agccaagacc cagtctcgtg agcagcagtt caacggcacc       540
```

```
taccgtgtgg tcagcgtcct ccccattgag caccaggact ggctcacagg gaaggagttc    600
aagtgcagag tcaaccacat agacctcccg tctcccatcg agaggaccat ctctaaggcc    660
agagggaggg cccataagcc cagtgtgtat gtcctgccgc catccccaaa ggagttgtca    720
tccagtgaca cagtcagcat cacctgcctg ataaaagact tctacccacc tgacattgat    780
gtggagtggc agagcaatgg acagcaggag cccgagagga agcaccgcat gaccccgccc    840
cagctggacg aggacgggtc ctacttcctg tacagcaagc tctctgtgga caagagccgc    900
tggcagcagg gagacccctt cacatgtgcg gtgatgcatg aaactctaca gaaccactac    960
acagatctat ccctctccca ttctccgggt aaacaggtgc cgcctcagta tcctccaatt   1020
caaagtatca gagtacaatt taccaggtgt gagaatgaga aggttgcat catcacatcc    1080 ccaagcaagg atgaaactat gaaggtgcaa gacaactcaa tcatcattaa ctgtgatggg   1140
ttttatctca tctccctgaa gggttacttc tctgaggagc tcagcctcag cctttattac   1200
cgaaagggtc ggggacccct cttctctctg agcaaggtca catctgttga ctccattgga   1260
gtggcctatc tggctttcaa ggacaaagtc tactttaatg tgaccactca cagtacctcc   1320
tacaaagaca tccaggtgaa tggtggggaa ttgattctca ttcatcaaaa tcctggtggc   1380
ttctgtgcct actga                                                    1395

<210> SEQ ID NO 2
<211> LENGTH: 698
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Leu Leu Leu Gly Ala Val Leu Leu Leu Ala Leu Pro Gly His
1               5                   10                  15

Asp Gln Glu Thr Thr Thr Gln Gly Pro Gly Val Leu Leu Pro Met Leu
            20                  25                  30

Leu Leu Gly Ala Val Leu Leu Leu Ala Leu Pro Gly His Asp Gln
        35                  40                  45

Glu Thr Thr Thr Gln Gly Pro Gly Val Leu Leu Pro Leu Pro Lys Gly
    50                  55                  60

Ala Cys Thr Gly Trp Met Ala Gly Ile Pro Gly His Pro Gly His Asn
65                  70                  75                  80

Gly Ala Pro Gly Arg Asp Gly Arg Asp Gly Leu Pro Lys Gly Ala Cys
                85                  90                  95

Thr Gly Trp Met Ala Gly Ile Pro Gly His Pro Gly His Asn Gly Ala
            100                 105                 110

Pro Gly Arg Asp Gly Arg Asp Gly Thr Pro Gly Glu Lys Gly Glu Lys
        115                 120                 125

Gly Asp Pro Gly Leu Ile Gly Pro Lys Gly Asp Ile Gly Glu Thr Gly
    130                 135                 140

Val Pro Gly Ala Glu Gly Thr Pro Gly Glu Lys Gly Glu Lys Gly Asp
145                 150                 155                 160

Pro Gly Leu Ile Gly Pro Lys Gly Asp Ile Gly Glu Thr Gly Val Pro
                165                 170                 175

Gly Ala Glu Gly Pro Arg Gly Phe Pro Gly Ile Gln Gly Arg Lys Gly
            180                 185                 190

Glu Pro Gly Asp Thr Pro Pro Cys Pro Val Pro Glu Pro Leu Gly Gly
        195                 200                 205
```

```
Pro Ser Asp Thr Pro Pro Cys Pro Val Pro Glu Pro Pro Arg Gly Phe
    210                 215                 220
Pro Gly Ile Gln Gly Arg Lys Gly Glu Pro Gly Val Leu Ile Phe Pro
225                 230                 235                 240
Pro Lys Pro Lys Asp Ile Leu Arg Ile Thr Arg Thr Pro Glu Val Thr
                245                 250                 255
Cys Val Val Leu Asp Leu Gly Arg Glu Asp Pro Glu Val Gln Ile Ser
                260                 265                 270
Trp Phe Val Asp Gly Lys Glu Val His Thr Ala Lys Thr Gln Ser Arg
        275                 280                 285
Glu Gln Gln Phe Asn Gly Thr Tyr Arg Val Val Ser Val Leu Pro Ile
    290                 295                 300
Glu His Gln Asp Trp Leu Thr Gly Lys Glu Phe Lys Cys Arg Val Asn
305                 310                 315                 320
His Ile Asp Leu Pro Ser Pro Ile Glu Arg Thr Ile Ser Lys Ala Arg
                325                 330                 335
Gly Arg Ala His Lys Pro Ser Val Tyr Val Leu Pro Pro Ser Pro Lys
                340                 345                 350
Glu Leu Ser Ser Ser Asp Thr Val Ser Ile Thr Cys Leu Ile Lys Asp
        355                 360                 365
Phe Tyr Pro Pro Asp Ile Asp Val Glu Trp Gln Ser Asn Gly Gln Gln
    370                 375                 380
Glu Pro Glu Arg Lys His Arg Met Thr Pro Gln Leu Asp Glu Asp
385                 390                 395                 400
Gly Ser Tyr Phe Leu Tyr Ser Lys Leu Ser Val Asp Lys Ser Arg Trp
                405                 410                 415
Gln Gln Gly Asp Pro Phe Thr Cys Ala Val Met His Glu Thr Leu Gln
                420                 425                 430
Asn His Tyr Thr Asp Leu Ser Leu Ser His Ser Pro Gly Lys Gln Val
        435                 440                 445
Pro Pro Gln Tyr Pro Pro Ile Gln Ser Ile Arg Val Gln Phe Thr Arg
    450                 455                 460
Cys Glu Asn Glu Lys Gly Cys Ile Ile Thr Ser Gln Val Pro Pro Gln
465                 470                 475                 480
Tyr Pro Pro Ile Gln Ser Ile Arg Val Gln Phe Thr Arg Cys Glu Asn
                485                 490                 495
Glu Lys Gly Cys Ile Ile Thr Ser Pro Ser Lys Asp Glu Thr Met Lys
                500                 505                 510
Val Gln Asp Asn Ser Ile Ile Ile Asn Cys Asp Gly Phe Tyr Leu Ile
        515                 520                 525
Ser Leu Lys Gly Tyr Phe Pro Ser Lys Asp Glu Thr Met Lys Val Gln
    530                 535                 540
Asp Asn Ser Ile Ile Ile Asn Cys Asp Gly Phe Tyr Leu Ile Ser Leu
545                 550                 555                 560
Lys Gly Tyr Phe Ser Glu Glu Leu Ser Leu Ser Leu Tyr Tyr Arg Lys
                565                 570                 575
Gly Arg Gly Pro Leu Phe Ser Leu Ser Lys Val Thr Ser Val Asp Ser
                580                 585                 590
Ile Gly Ser Glu Glu Leu Ser Leu Ser Leu Tyr Tyr Arg Lys Gly Arg
        595                 600                 605
Gly Pro Leu Phe Ser Leu Ser Lys Val Thr Ser Val Asp Ser Ile Gly
    610                 615                 620
```

```
Val Ala Tyr Leu Ala Phe Lys Asp Lys Val Tyr Phe Asn Val Thr Thr
625                 630                 635                 640

His Ser Thr Ser Tyr Lys Asp Ile Gln Val Asn Gly Gly Glu Val Ala
                645                 650                 655

Tyr Leu Ala Phe Lys Asp Lys Val Tyr Phe Asn Val Thr Thr His Ser
            660                 665                 670

Thr Ser Tyr Lys Asp Ile Gln Val Asn Gly Gly Glu Leu Ile Leu Ile
        675                 680                 685

His Gln Asn Pro Gly Gly Phe Cys Ala Tyr
    690                 695
```

<210> SEQ ID NO 3
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Met Leu Leu Leu Gly Ala Val Leu Leu Leu Ala Leu Pro Gly His
1               5                   10                  15

Asp Gln Glu Thr Thr Gln Gly Pro Gly Val Leu Leu Pro Leu Pro
                20                  25                  30

Lys Gly Ala Cys Thr Gly Trp Met Ala Gly Ile Pro Gly His Pro Gly
            35                  40                  45

His Asn Gly Ala Pro Gly Arg Asp Gly Arg Asp Gly Thr Pro Gly Glu
        50                  55                  60

Lys Gly Glu Lys Gly Asp Pro Gly Leu Ile Gly Pro Lys Gly Asp Ile
65                  70                  75                  80

Gly Glu Thr Gly Val Pro Gly Ala Glu Gly Pro Arg Gly Phe Pro Gly
                85                  90                  95

Ile Gln Gly Arg Lys Gly Glu Pro Gly Asp Thr Pro Pro Cys Pro Val
            100                 105                 110

Pro Glu Pro Leu Gly Gly Pro Ser Val Leu Ile Phe Pro Pro Lys Pro
        115                 120                 125

Lys Asp Ile Leu Arg Ile Thr Arg Thr Pro Glu Val Thr Cys Val Val
130                 135                 140

Leu Asp Leu Gly Arg Glu Asp Pro Glu Val Gln Ile Ser Trp Phe Val
145                 150                 155                 160

Asp Gly Lys Glu Val His Thr Ala Lys Thr Gln Ser Arg Glu Gln Gln
                165                 170                 175

Phe Asn Gly Thr Tyr Arg Val Val Ser Val Leu Pro Ile Glu His Gln
            180                 185                 190

Asp Trp Leu Thr Gly Lys Glu Phe Lys Cys Arg Val Asn His Ile Asp
        195                 200                 205

Leu Pro Ser Pro Ile Glu Arg Thr Ile Ser Lys Ala Arg Gly Arg Ala
    210                 215                 220

His Lys Pro Ser Val Tyr Val Leu Pro Pro Ser Pro Lys Glu Leu Ser
225                 230                 235                 240

Ser Ser Asp Thr Val Ser Ile Thr Cys Leu Ile Lys Asp Phe Tyr Pro
                245                 250                 255

Pro Asp Ile Asp Val Glu Trp Gln Ser Asn Gly Gln Gln Glu Pro Glu
            260                 265                 270

Arg Lys His Arg Met Thr Pro Pro Gln Leu Asp Glu Asp Gly Ser Tyr
        275                 280                 285
```

Phe Leu Tyr Ser Lys Leu Ser Val Asp Lys Ser Arg Trp Gln Gln Gly
            290                 295                 300

Asp Pro Phe Thr Cys Ala Val Met His Glu Thr Leu Gln Asn His Tyr
305                 310                 315                 320

Thr Asp Leu Ser Leu Ser His Ser Pro Gly Lys Gln Val Pro Pro Gln
                325                 330                 335

Tyr Pro Pro Ile Gln Ser Ile Arg Val Gln Phe Thr Arg Cys Glu Asn
            340                 345                 350

Glu Lys Gly Cys Ile Ile Thr Ser Pro Ser Lys Asp Glu Thr Met Lys
        355                 360                 365

Val Gln Asp Asn Ser Ile Ile Ile Asn Cys Asp Gly Phe Tyr Leu Ile
    370                 375                 380

Ser Leu Lys Gly Tyr Phe Ser Glu Glu Leu Ser Leu Ser Leu Tyr Tyr
385                 390                 395                 400

Arg Lys Gly Arg Gly Pro Leu Phe Ser Leu Ser Lys Val Thr Ser Val
                405                 410                 415

Asp Ser Ile Gly Val Ala Tyr Leu Ala Phe Lys Asp Lys Val Tyr Phe
            420                 425                 430

Asn Val Thr Thr His Ser Thr Ser Tyr Lys Asp Ile Gln Val Asn Gly
        435                 440                 445

Gly Glu Leu Ile Leu Ile His Gln Asn Pro Gly Gly Phe Cys Ala Tyr
    450                 455                 460

<210> SEQ ID NO 4
<211> LENGTH: 5
<212> TYPE: DNA
<213> ORGANISM: Unknown
<220> FEATURE:
<223> OTHER INFORMATION: Description of Unknown: CpG flanking
      region oligonucleotide

<400> SEQUENCE: 4 tcgtt                                                               5

<210> SEQ ID NO 5
<211> LENGTH: 5
<212> TYPE: DNA
<213> ORGANISM: Unknown
<220> FEATURE:
<223> OTHER INFORMATION: Description of Unknown: CpG flanking
      region oligonucleotide

<400> SEQUENCE: 5 tcgta                                                               5

<210> SEQ ID NO 6
<211> LENGTH: 9
<212> TYPE: DNA
<213> ORGANISM: Unknown
<220> FEATURE:
<223> OTHER INFORMATION: Description of Unknown: Immunostimulatory
      motif oligonucleotide

<400> SEQUENCE: 6 tcgtcgttt                                                           9